US010052149B2

(12) United States Patent
Germain et al.

(10) Patent No.: US 10,052,149 B2
(45) Date of Patent: Aug. 21, 2018

(54) ARTHROSCOPIC DEVICES AND METHODS

(71) Applicant: RELIGN Corporation, Cupertino, CA (US)

(72) Inventors: Aaron Germain, San Jose, CA (US); Jeff Norton, Emerald Hills, CA (US); Jan Echeverry, San Jose, CA (US); Evan Nessim, Los Gatos, CA (US); Sal Mangano, San Jose, CA (US)

(73) Assignee: RELIGN Corporation, Campbell, CA (US)

( * ) Notice: Subject to any disclaimer, the term of this patent is extended or adjusted under 35 U.S.C. 154(b) by 0 days.

(21) Appl. No.: 15/410,723

(22) Filed: Jan. 19, 2017

(65) Prior Publication Data

US 2017/0202612 A1   Jul. 20, 2017

Related U.S. Application Data

(60) Provisional application No. 62/280,844, filed on Jan. 20, 2016, provisional application No. 62/324,498, filed on Apr. 19, 2016.

(51) Int. Cl.
*A61B 18/12* (2006.01)
*A61B 18/14* (2006.01)
(Continued)

(52) U.S. Cl.
CPC ......... *A61B 18/1482* (2013.01); *A61B 34/25* (2016.02); *A61B 2018/00208* (2013.01); *A61B 2018/00565* (2013.01); *A61B 2018/00577* (2013.01); *A61B 2018/00589* (2013.01); *A61B 2018/00601* (2013.01); *A61B 2018/00779* (2013.01); *A61B 2018/048* (2013.01); *A61B 2018/1412* (2013.01); *A61B 2218/007* (2013.01)

(58) Field of Classification Search
CPC ...... A61B 18/1482; A61B 2018/00601; A61B 2018/00565; A61B 2018/00577; A61B 2018/00589; A61B 2018/00208; A61B 2018/1412; A61B 2018/00779; A61B 2018/0048; A61B 2218/007; A61B 34/25
See application file for complete search history.

(56) References Cited

U.S. PATENT DOCUMENTS 5,456,689 A * 10/1995 Kresch ............... A61B 18/1485
604/22
5,653,684 A * 8/1997 Laptewicz ......... A61B 18/1492
604/107

(Continued)

OTHER PUBLICATIONS

Co-pending U.S. Appl. No. 15/488,270, filed Apr. 14, 2017.

(Continued)

*Primary Examiner* — Daniel Fowler
(74) *Attorney, Agent, or Firm* — Wilson Sonsini Goodrich & Rosati

(57) ABSTRACT

An electrosurgical probe for ablating tissue includes an elongated shaft having an axis and a distal end. An electrically insulating housing at the distal end of the shaft has a window, and an interior channel in the shaft extends through the housing to the window. The window faces laterally relative to the axis, and a moveable member with a blade-like electrode edge is disposed within the window. A motor drives the energized electrode edge axially in the window to ablate tissue.

29 Claims, 30 Drawing Sheets

(51) Int. Cl.
    *A61B 18/00*            (2006.01)
    *A61B 18/04*            (2006.01)
    *A61B 34/00*            (2016.01)

(56) References Cited

U.S. PATENT DOCUMENTS

| | | | | |
|---|---|---|---|---|
| 6,214,003 B1 * | 4/2001 | Morgan | ............... | A61B 18/148 |
| | | | | 606/41 |
| 6,491,690 B1 * | 12/2002 | Goble | .................. | A61B 18/148 |
| | | | | 604/22 |
| 7,150,747 B1 * | 12/2006 | McDonald | ........... | A61B 18/148 |
| | | | | 606/180 |
| 2002/0183742 A1 * | 12/2002 | Carmel | ................ | A61B 18/148 |
| | | | | 606/41 |
| 2003/0065321 A1 * | 4/2003 | Carmel | .............. | A61B 18/1402 |
| | | | | 606/41 |

OTHER PUBLICATIONS

Office Action dated Mar. 9, 2017 for U.S. Appl. No. 15/091,402.
Office Action dated Apr. 5, 2017 for U.S. Appl. No. 13/857,068.
Office Action dated Apr. 18, 2017 for U.S. Appl. No. 14/657,684.

* cited by examiner

ARTHROSCOPIC DEVICES AND METHODS

CROSS-REFERENCE TO RELATED APPLICATIONS

This application claims the benefit of Provisional Application No. 62/280,844, filed on Jan. 20, 2016, and Provisional Application No. 62/324,498, filed on Apr. 19, 2016, the full disclosures of which are incorporated herein by reference.

BACKGROUND OF THE INVENTION

1. Field of the Invention

This invention relates to arthroscopic tissue cutting and ablation devices by which anatomical tissues may be resected, ablated and removed from a joint or other site. More specifically, this invention relates to electrosurgical probes and methods for ablating and removing soft tissue.

2. Description of the Background Art

In many arthroscopic procedures including subacromial decompression, anterior cruciate ligament reconstruction, and resection of the acromioclavicular joint, there is a need for cutting and removing and soft tissue. Currently, surgeons use arthroscopic shavers having rotational cutting surfaces to remove soft tissue in such procedures.

The need exists for arthroscopic instrument that remove soft tissue rapidly.

SUMMARY OF THE INVENTION

In a first aspect, the present invention provides apparatus such as electrosurgical probes. In exemplary embodiments, an electrosurgical probe comprises an elongated shaft assembly having a proximal end, a distal end, and a longitudinal axis. A distal housing is mounted on the distal end of the shaft and has a laterally open window, that is, a plane of the window is generally parallel to or aligned with the longitudinal axis of the shaft. An interior channel extends axially through the shaft and extends through an interior of the housing to a window in the housing. An electrode member with an elongate edge extends laterally cross the window and is configured to reciprocate the elongate edge longitudinally relative to the window.

In specific embodiments, the shaft may comprise an outer sleeve and an inner sleeve, and the distal housing may be a ceramic and is mounted on a distal end of the outer sleeve. The electrode member is mounted on a distal end of the inner sleeve, and the inner sleeve may be reciprocatably mounted in the outer sleeve. A proximal hub is attached to a proximal end of the outer sleeve and a sliding collar is coupled to a proximal end of the inner sleeve, the sliding collar being mounted and configured to axially reciprocate within the proximal hub while being restrained from rotation relative to the proximal hub. In particular examples, a rotating drive coupling is mounted to rotate in the proximal hub while being restrained from axially translating relative to the proximal hub. The rotating drive coupling can have a distal surface which engages a proximal surface on the sliding collar, and the distal and proximal surfaces may have cam surfaces or otherwise shaped so that rotation and/or rotational oscillation of the rotating coupling causes the sliding collar to axially reciprocate within the proximal hub which in turn will cause the elongate edge of the electrode member to axially reciprocate relative to the window in the distal housing.

While the dimensions and geometries of the probe are usually not critical, in specific designs, the electrode member may reciprocate with a stroke in a range from 0.01 mm and 10 mm, often being in a range between 0.1 mm and 5 mm. The elongate edge may be substantially flush with a plane of the window or in other instances may protrude outwardly from a plane of the window. When protruding, the electrode edge may protrude outwardly from the plane of the window by distance in a range from 0.50 mm to 2.5 mm. Further, the electrode edges may be configured to extend over edges or the window during reciprocation.

The electrosurgical probes of the present invention may further comprise a handpiece and motor drive operatively coupled to the shaft and configured to axially reciprocate the electrode at high speed relative to the window to provide a method of dynamic ablation. Usually, a proximal hub is connected to the proximal end of the elongated shaft, and the handpiece and motor drive are detachably coupled to the proximal hub. A negative pressure source is provided for coupling through the handpiece and proximal hub to an interior channel of the shaft which communicates with the window in the distal housing. The motor drive is typically configured to axially reciprocate the electrode edge at a rate in a range from 1 Hz and 1,000 Hz.

The distal housing may have a variety of specific geometries, but will typically comprises a somewhat L-shaped body with a shank region attached to the distal end of the shaft and a lateral region with an open end defining the laterally open window. The open end of the lateral region typically defines a rectangular window with a planar opening that communicates with an interior channel in the housing and the shaft. In specific embodiments, the shaft may be cylindrical and the shank region may have a cylindrical shape to conform to the cylindrical shaft. The reciprocating component that carries the electrode member may also have an L-shaped geometry with an axial region extending through the shank region of the distal housing and a lateral region terminating in the elongate member configured for reciprocation in the window, and the shaft may comprise an outer sleeve and an inner sleeve. When the distal housing and the reciprocating component both have L-shaped geometries, the shank region of the distal housing may be mounted on a distal end of the outer sleeve and the electrode member may mounted on a distal end of the inner sleeve, and the inner sleeve may be reciprocatably mounted in the outer sleeve.

In a first aspect, the present invention provides a method for ablating tissue. The method comprises engaging a window having a planar opening in a housing against a surface of the tissue. An elongate edge of an electrode member may be reciprocated across the window in a plane parallel to the plane of the window, and a radiofrequency current with a cutting waveform may be applied to the electrode member to dynamically ablate tissue and generate tissue debris. A vacuum may be applied to the interior channel in the housing to aspirate the tissue debris through window.

In some embodiments, the elongate edge of the electrode member may protrude beyond the plane of the window in the housing, while in other embodiments the edge may be flushed with or recessed into the plane. When protruding, the edge may protrude beyond the plane of the window in the housing by a distance in the range from 0.50 mm to 2.5 mm. The electrode member is typically reciprocated at a rate in a range from 1 Hz and 1,000 Hz, usually between 1 Hz and 500 Hz.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to devices for cutting, ablating and removing bone and soft tissue and related methods of use. Several variations of the invention will now be described to provide an overall understanding of the principles of the form, function and methods of use of the devices disclosed herein. In one variation, the present disclosure provides for an arthroscopic cutter or burr assembly for cutting or abrading bone that is disposable and is configured for detachable coupling to a non-disposable handle and motor drive component. This description of the general principles of this invention is not meant to limit the inventive concepts in the appended claims.

In general, one embodiment provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds ranging from 3,000 RPM to 20,000 RPM.

Figure 1:
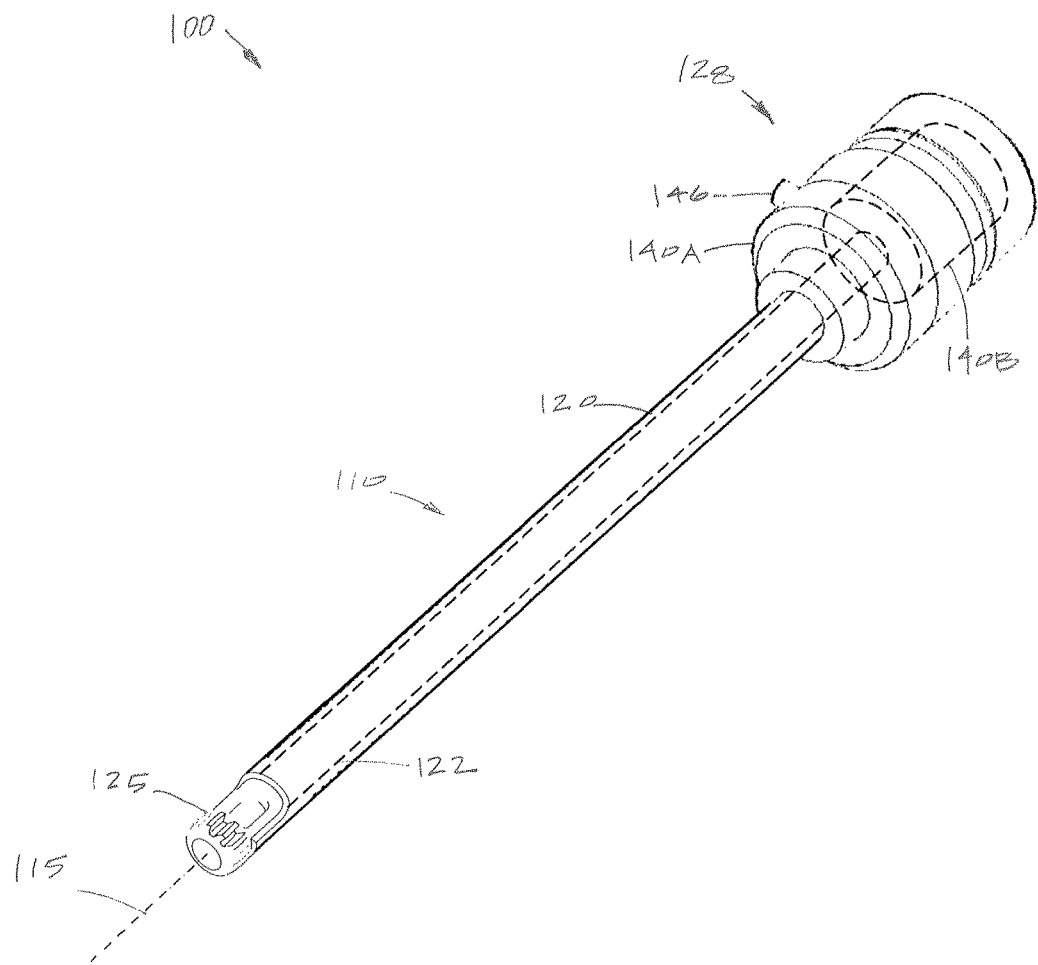
FIG. 1 is a perspective view of a disposable arthroscopic cutter or burr assembly with a ceramic cutting member carried at the distal end of a rotatable inner sleeve with a window in the cutting member proximal to the cutting edges of the burr.
Figure 2:
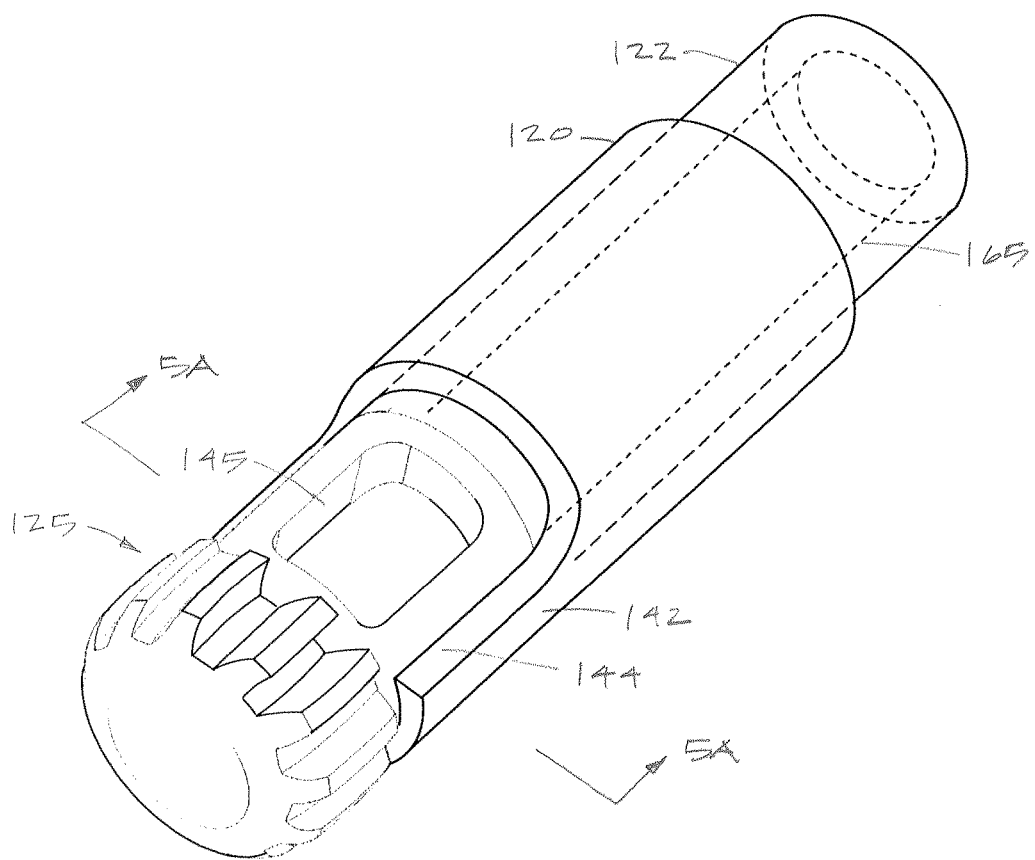
FIG. 2 is an enlarged perspective view of the ceramic cutting member of the arthroscopic cutter or burr assembly of FIG. 1.

In one variation shown in FIGS. 1-2, an arthroscopic cutter or burr assembly 100 is provided for cutting and removing hard tissue, which operates in a manner similar to commercially available metals shavers and burrs. FIG. 1 shows disposable burr assembly 100 that is adapted for detachable coupling to a handle 104 and motor drive unit 105 therein as shown in FIG. 3.

The cutter assembly 100 has a shaft 110 extending along longitudinal axis 115 that comprises an outer sleeve 120 and an inner sleeve 122 rotatably disposed therein with the inner sleeve 122 carrying a distal ceramic cutting member 125. The shaft 110 extends from a proximal hub assembly 128 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 3). The outer and inner sleeves 120 and 122 typically can be a thin wall stainless steel tube, but other materials can be used such as ceramics, metals, plastics or combinations thereof.

Referring to FIG. 2, the outer sleeve 120 extends to distal sleeve region 142 that has an open end and cut-out 144 that is adapted to expose a window 145 in the ceramic cutting member 125 during a portion of the inner sleeve's rotation. Referring to FIGS. 1 and 3, the proximal hub 128 of the burr assembly 100 is configured with a J-lock, snap-fit feature, screw thread or other suitable feature for detachably locking the hub assembly 128 into the handle 104. As can be seen in FIG. 1, the outer hub 140A includes a projecting key 146 that is adapted to mate with a receiving J-lock slot 148 in the handle 104 (see FIG. 3).

Figure 3:
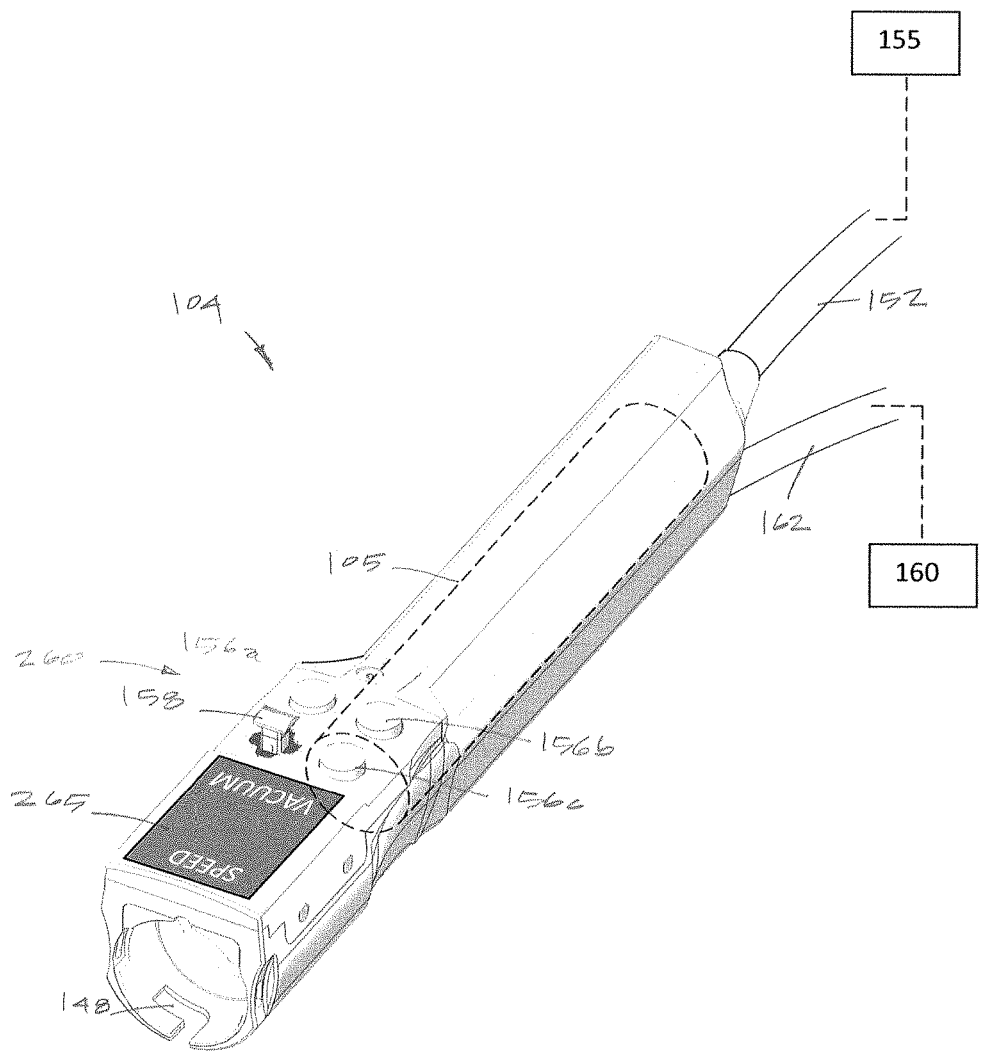
FIG. 3 is a perspective view of a handle body with a motor drive unit to which the burr assembly of FIG. 1 can be coupled, with the handle body including an LCD screen for displaying operating parameters of device during use together with a joystick and mode control actuators on the handle.

In FIG. 3, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 be moved forward and backward to adjust the rotational speed of the ceramic cutting member 125. The rotational speed of the cutter can continuously adjustable, or can be adjusted in increments up to 20,000 RPM. FIG. 3 further shows that negative pressure source 160 is coupled to aspiration tubing 162 which communicates with a flow channel in the handle 104 and lumen 165 in inner sleeve 122 which extends to window 145 in the ceramic cutting member 125 (FIG. 2).

Figure 4:
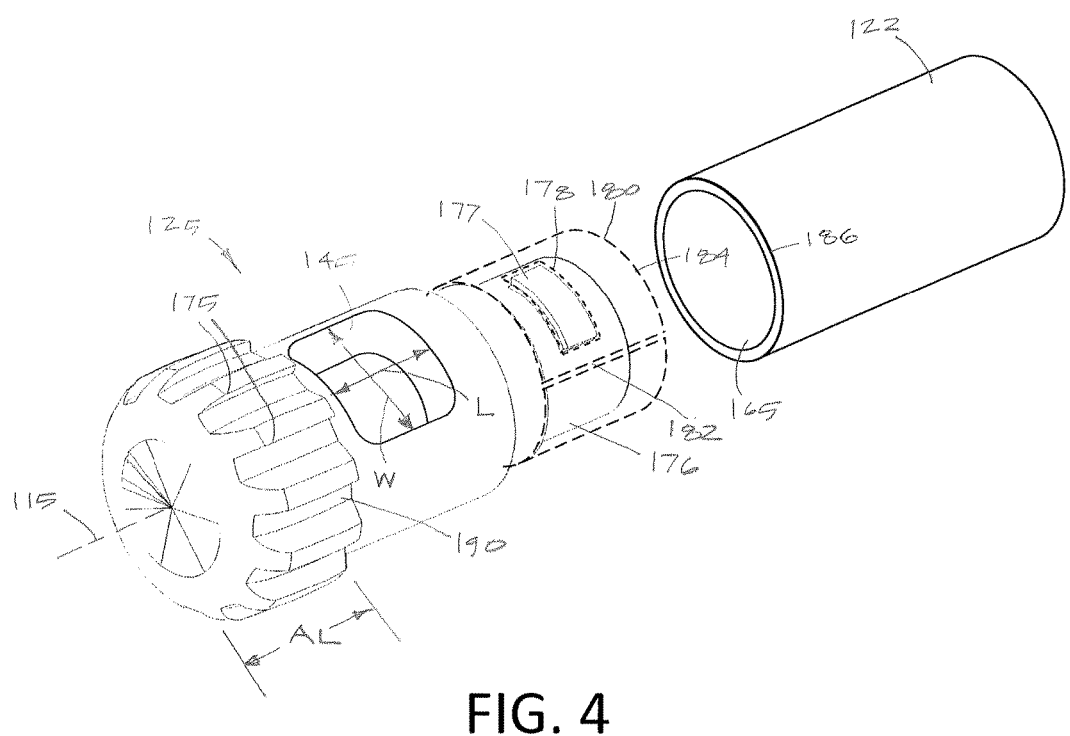
FIG. 4 is an enlarged perspective view of the ceramic cutting member showing a manner of coupling the cutter to a distal end of the inner sleeve of the burr assembly.

Now referring to FIGS. 2 and 4, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in MPam$^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel provides ductile behavior which results in rapid cleaving and wear on sharp edges of a stainless steel cutting member. In contrast, technical ceramic materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

CHART A

| | Hardness (GPa) | Fracture Toughness (MPam$^{1/2}$) | Ratio Hardness to Fracture Toughness |
|---|---|---|---|
| Cortical bone | 0.8 | 12 | .07:1 |
| Stainless steel 304 | 2.1 | 228 | .01:1 |
| Yttria-stabilized zirconia (YTZP) | | | |
| YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) Magnesia stabilized zirconia (MSZ) | 13.0 | 13 | 1.00:1 |
| Dura-Z ® (Superior Technical Ceramics) | 12.0 | 11 | 1.09:1 |
| MSZ 200 (CoorsTek) Zirconia toughened alumina (ZTA) | 11.7 | 12 | 0.98:1 |
| YTA-14 (Superior Technical Ceramics) | 14.0 | 5 | 2.80:1 |
| ZTA (CoorsTek) Ceria stabilized zirconia | 14.8 | 6 | 2.47:1 |
| CSZ (Superior Technical Ceramics) Silicon Nitride | 11.7 | 12 | 0.98:1 |
| SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics— Electric and Magnetic Ceramics, Bioceramics, Ceramics and Environment* (2011).

In one variation, the ceramic cutting member 125 is fabricated of an yttria-stabilized zirconia as is known in the field of technical ceramics, and can be provided by CoorsTek Inc., 16000 Table Mountain Pkwy., Golden, Colo. 80403 or Superior Technical Ceramics Corp., 600 Industrial Park Rd., St. Albans City, Vt. 05478. Other technical ceramics that may be used consist of magnesia-stabilized zirconia, ceria-stabilized zirconia, zirconia toughened alumina and silicon nitride. In general, in one aspect of the invention, the monolithic ceramic cutting member 125 has a hardness rating of at least 8 Gpa (kg/mm$^2$). In another aspect of the invention, the ceramic cutting member 125 has a fracture toughness of at least 2 MPam$^{1/2}$.

The fabrication of such ceramics or monoblock components are known in the art of technical ceramics, but have not been used in the field of arthroscopic or endoscopic cutting or resecting devices. Ceramic part fabrication includes molding, sintering and then heating the molded part at high temperatures over precise time intervals to transform a compressed ceramic powder into a ceramic monoblock which can provide the hardness range and fracture toughness range as described above. In one variation, the molded ceramic member part can have additional strengthening through hot isostatic pressing of the part. Following the ceramic fabrication process, a subsequent grinding process optionally may be used to sharpen the cutting edges 175 of the burr (see FIGS. 2 and 4).

In FIG. 4, it can be seen that in one variation, the proximal shaft portion 176 of cutting member 125 includes projecting elements 177 which are engaged by receiving openings 178 in a stainless steel split collar 180 shown in phantom view. The split collar 180 can be attached around the shaft portion 176 and projecting elements 177 and then laser welded along weld line 182. Thereafter, proximal end 184 of collar 180 can be laser welded to the distal end 186 of stainless steel inner sleeve 122 to mechanically couple the ceramic body 125 to the metal inner sleeve 122. In another aspect of the invention, the ceramic material is selected to have a coefficient of thermal expansion between is less than 10 (1×10$^6$/° C.) which can be close enough to the coefficient of thermal expansion of the metal sleeve 122 so that thermal stresses will be reduced in the mechanical coupling of the ceramic member 125 and sleeve 122 as just described. In another variation, a ceramic cutting member can be coupled to metal sleeve 122 by brazing, adhesives, threads or a combination thereof.

Referring to FIGS. 1 and 4, the ceramic cutting member 125 has window 145 therein which can extend over a radial angle of about 10° to 90° of the cutting member's shaft. In the variation of FIG. 1, the window is positioned proximally to the cutting edges 175, but in other variations, one or more windows or openings can be provided and such openings can extend in the flutes 190 (see FIG. 6) intermediate the cutting edges 175 or around a rounded distal nose of the ceramic cutting member 125. The length L of window 145 can range from 2 mm to 10 mm depending on the diameter and design of the ceramic member 125, with a width W of 1 mm to 10 mm.

Figure 6:
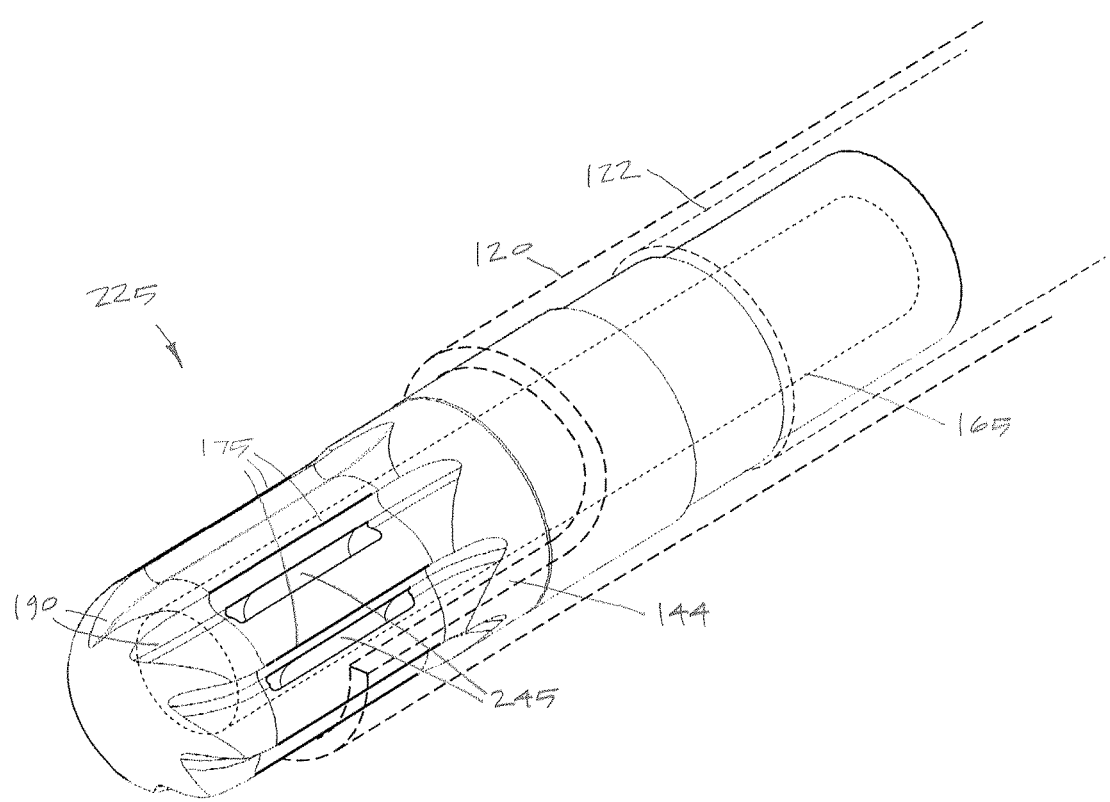
FIG. 6 is a perspective view of another ceramic cutting member carried at the distal end of an inner sleeve with a somewhat rounded distal nose and deeper flutes than the cutting member of FIGS. 2 and 4, and with aspiration openings or ports formed in the flutes.
Figure 7:
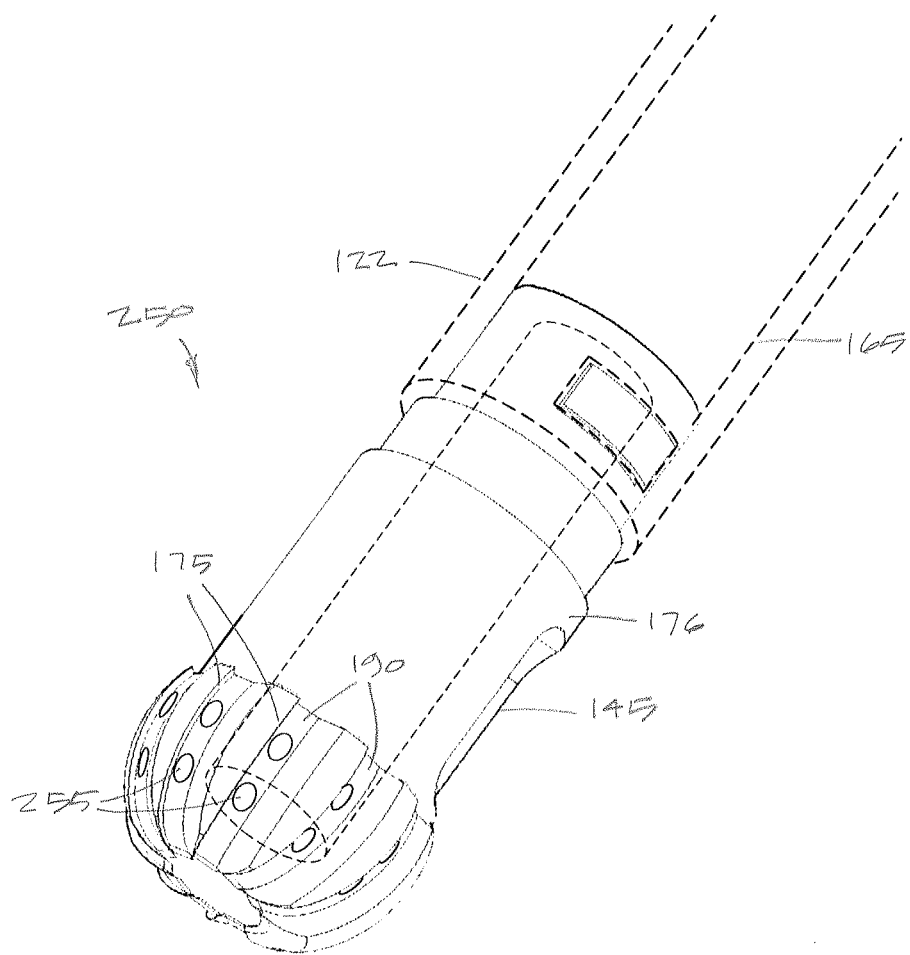
FIG. 7 is a perspective view of another ceramic cutting member with cutting edges that extend around a distal nose of the cutter together with an aspiration window in the shaft portion and aspiration openings in the flutes.

FIGS. 1 and 4 shows the ceramic burr or cutting member 125 with a plurality of sharp cutting edges 175 which can extend helically, axially, longitudinally or in a cross-hatched configuration around the cutting member, or any combination thereof. The number of cutting edges 175 ands intermediate flutes 190 can range from 2 to 100 with a flute depth ranging from 0.10 mm to 2.5 mm. In the variation shown in FIGS. 2 and 4, the outer surface or periphery of the cutting edges 175 is cylindrical, but such a surface or periphery can be angled relative to axis 115 or rounded as shown in FIGS. 6 and 7. The axial length AL of the cutting edges can range between 1 mm and 10 mm. While the cutting edges 175 as depicted in FIG. 4 are configured for optimal bone cutting or abrading in a single direction of rotation, it should be appreciated the that the controller 155 and motor drive 105 can be adapted to rotate the ceramic cutting member 125 in either rotational direction, or oscillate the cutting member back and forth in opposing rotational directions.

Figure 5A:
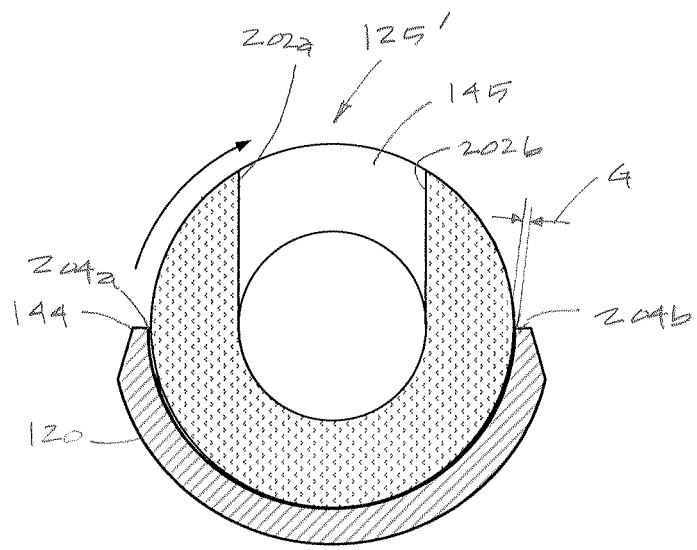
FIG. 5A is a cross-sectional view of a cutting assembly similar to that of FIG. 2 taken along line 5A-5A showing the close tolerance between sharp cutting edges of a window in a ceramic cutting member and sharp lateral edges of the outer sleeve which provides a scissor-like cutting effect in soft tissue.
Figure 5B:
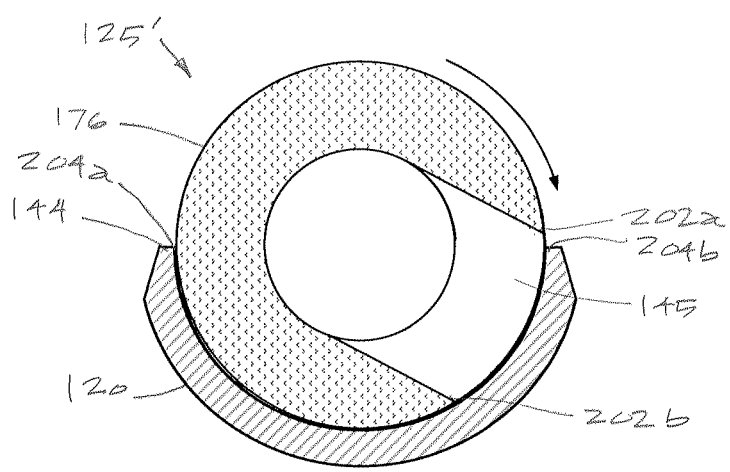
FIG. 5B is a cross-sectional view of the cutting assembly of FIG. 5A with the ceramic cutting member in a different rotational position than in FIG. 5A.

FIGS. 5A-5B illustrate a sectional view of the window 145 and shaft portion 176 of a ceramic cutting member 125' that is very similar to the ceramic member 125 of FIGS. 2 and 4. In this variation, the ceramic cutting member has window 145 with one or both lateral sides configured with sharp cutting edges 202a and 202b which are adapted to resect tissue when rotated or oscillated within close proximity, or in scissor-like contact with, the lateral edges 204a and 204b of the sleeve walls in the cut-out portion 144 of the distal end of outer sleeve 120 (see FIG. 2). Thus, in general, the sharp edges of window 145 can function as a cutter or shaver for resecting soft tissue rather than hard tissue or bone. In this variation, there is effectively no open gap G between the sharp edges 202a and 202b of the ceramic cutting member 125' and the sharp lateral edges 204a, 204b of the sleeve 120. In another variation, the gap G between the window cutting edges 202a, 202b and the sleeve edges 204a, 204b is less than about 0.020", or less than 0.010".

FIG. 6 illustrates another variation of ceramic cutting member 225 coupled to an inner sleeve 122 in phantom view. The ceramic cutting member again has a plurality of sharp cutting edges 175 and flutes 190 therebetween. The outer sleeve 120 and its distal opening and cut-out shape 144 are also shown in phantom view. In this variation, a plurality of windows or opening 245 are formed within the flutes 190 and communicate with the interior aspiration channel 165 in the ceramic member as described previously.

FIG. 7 illustrates another variation of ceramic cutting member 250 coupled to an inner sleeve 122 (phantom view) with the outer sleeve not shown. The ceramic cutting member 250 is very similar to the ceramic cutter 125 of FIGS. 1, 2 and 4, and again has a plurality of sharp cutting edges 175 and flutes 190 therebetween. In this variation, a plurality of windows or opening 255 are formed in the flutes 190 intermediate the cutting edges 175 and another window 145 is provided in a shaft portion 176 of ceramic member 225 as described previously. The openings 255 and window 145 communicate with the interior aspiration channel 165 in the ceramic member as described above.

It can be understood that the ceramic cutting members can eliminate the possibility of leaving metal particles in a treatment site. In one aspect of the invention, a method of preventing foreign particle induced inflammation in a bone treatment site comprises providing a rotatable cutter fabricated of a ceramic material having a hardness of at least 8 Gpa (kg/mm$^2$) and/or a fracture toughness of at least 2 MPam$^{1/2}$ and rotating the cutter to cut bone without leaving any foreign particles in the treatment site. The method includes removing the cut bone tissue from the treatment site through an aspiration channel in a cutting assembly.

Figure 8:
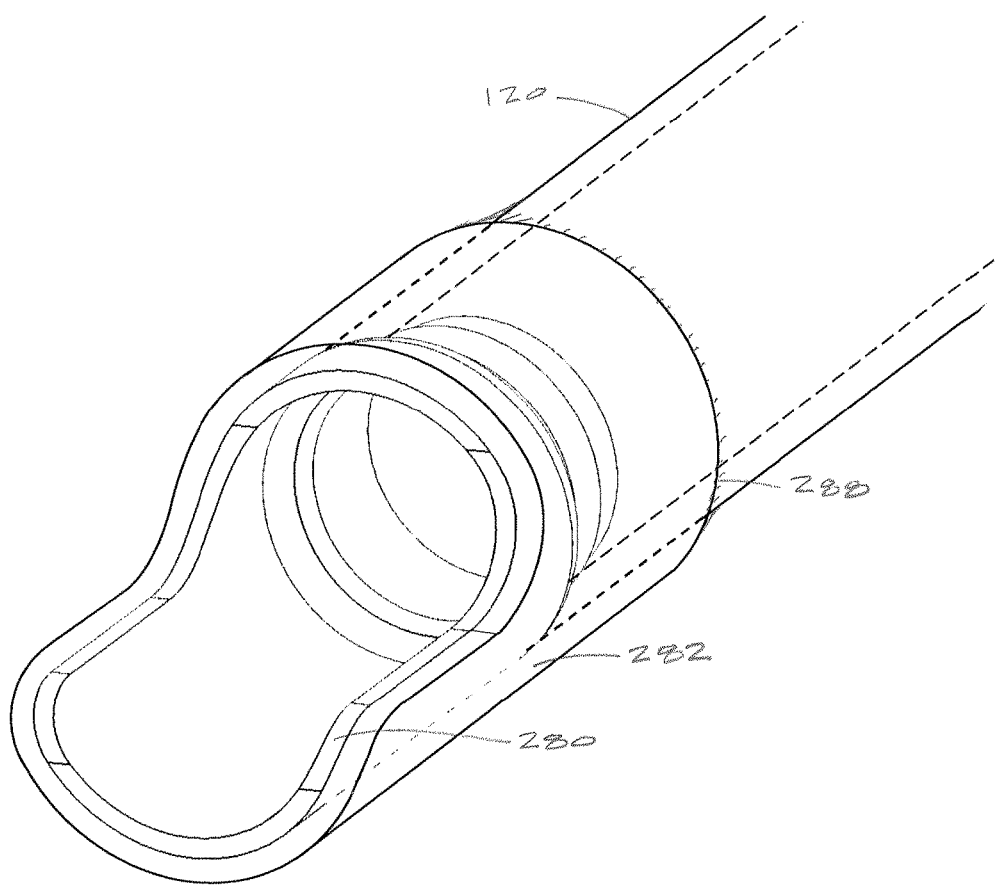
FIG. 8 is a perspective view of a ceramic housing carried at the distal end of the outer sleeve.

FIG. 8 illustrates variation of an outer sleeve assembly with the rotating ceramic cutter and inner sleeve not shown. In the previous variations, such as in FIGS. 1, 2 and 6, shaft portion 176 of the ceramic cutter 125 rotates in a metal outer sleeve 120. FIG. 8 illustrates another variation in which a ceramic cutter (not shown) would rotate in a ceramic housing 280. In this variation, the shaft or a ceramic cutter would thus rotate is a similar ceramic body which may be advantageous when operating a ceramic cutter at high rotational speeds. As can be seen in FIG. 8, a metal distal metal housing 282 is welded to the outer sleeve 120 along weld line 288. The distal metal housing 282 is shaped to support and provide strength to the inner ceramic housing 282.

Figure 9:
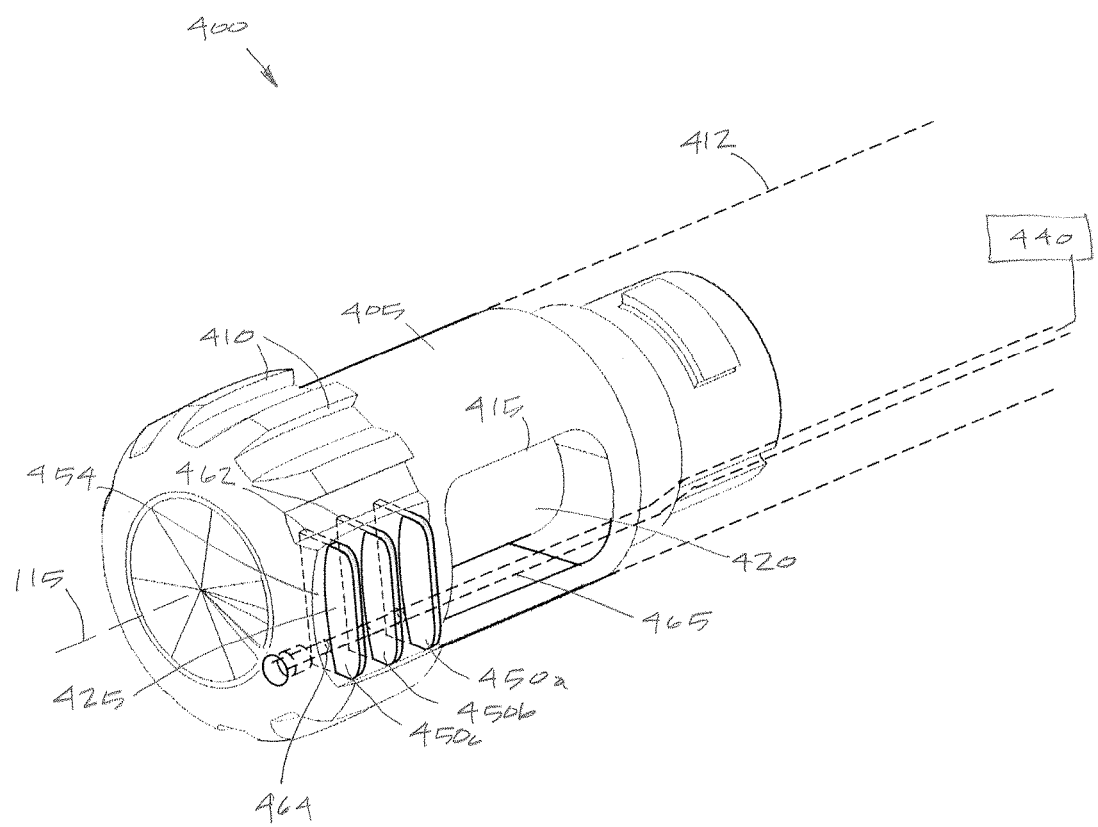
FIG. 9 is a perspective of another variation of a ceramic member with cutting edges that includes an aspiration window and an electrode arrangement positioned distal to the window.
Figure 10:
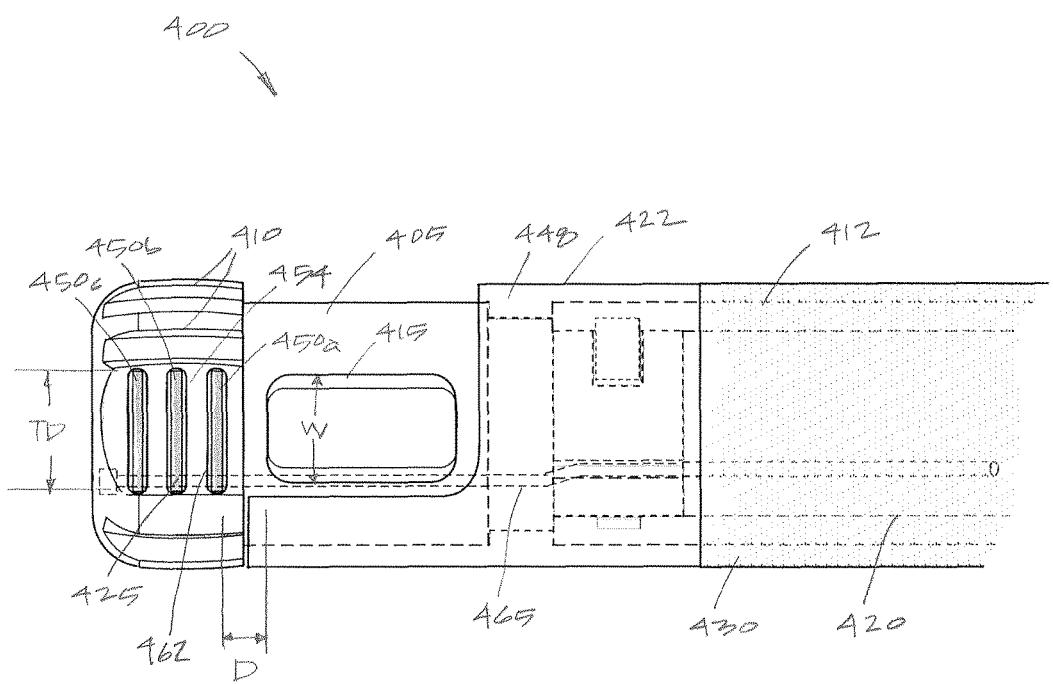
FIG. 10 is an elevational view of a ceramic member and shaft of FIG. 9 showing the width and position of the electrode arrangement in relation to the window.
Figure 11:
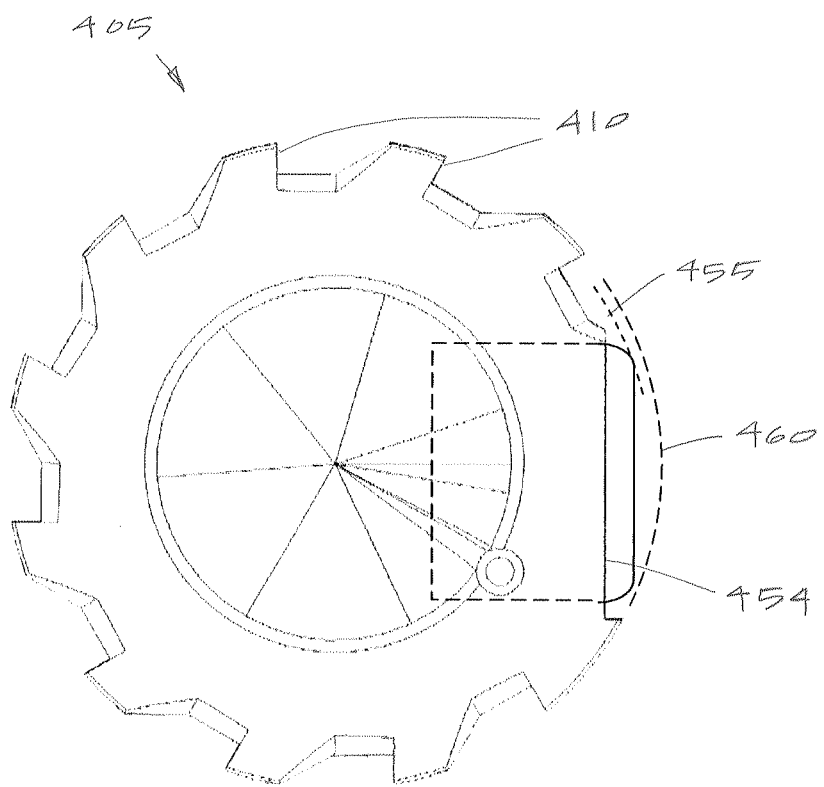
FIG. 11 is an end view of a ceramic member of FIGS. 9-10 the outward periphery of the electrode arrangement in relation to the rotational periphery of the cutting edges of the ceramic member.

FIGS. 9-11 are views of an alternative tissue resecting assembly or working end 400 that includes a ceramic member 405 with cutting edges 410 in a form similar to that described previously. FIG. 9 illustrates the monolithic ceramic member 405 carried as a distal tip of a shaft or inner sleeve 412 as described in previous embodiments. The ceramic member 405 again has a window 415 that communicates with aspiration channel 420 in shaft 412 that is connected to negative pressure source 160 as described previously. The inner sleeve 412 is operatively coupled to a motor drive 105 and rotates in an outer sleeve 422 of the type shown in FIG. 2. The outer sleeve 422 is shown in FIG. 10.

In the variation illustrated in FIG. 9, the ceramic member 405 carries an electrode arrangement 425, or active electrode, having a single polarity that is operatively connected to an RF source 440. A return electrode, or second polarity electrode 430, is provided on the outer sleeve 422 as shown in FIG. 10. In one variation, the outer sleeve 422 can comprise an electrically conductive material such as stainless steel to thereby function as return electrode 445, with a distal portion of outer sleeve 422 is optionally covered by a thin insulative layer 448 such as parylene, to space apart the active electrode 425 from the return electrode 430.

The active electrode arrangement 425 can consist of a single conductive metal element or a plurality of metal elements as shown in FIGS. 9 and 10. In one variation shown in FIG. 9, the plurality of electrode elements 450a, 450b and 450c extend transverse to the longitudinal axis 115 of ceramic member 405 and inner sleeve 412 and are slightly spaced apart in the ceramic member. In one variation shown in FIGS. 9 and 10, the active electrode 425 is spaced distance D from the distal edge 452 of window 415 which is less than 5 mm and often less than 2 mm for reasons described below. The width W and length L of window 415 can be the same as described in a previous embodiment with reference to FIG. 4.

As can be seen in FIGS. 9 and 11, the electrode arrangement 425 is carried intermediate the cutting edges 410 of the ceramic member 405 in a flattened region 454 where the cutting edges 410 have been removed. As can be best understood from FIG. 11, the outer periphery 455 of active electrode 425 is within the cylindrical or rotational periphery of the cutting edges 410 when they rotate. In FIG. 11, the rotational periphery of the cutting edges is indicated at 460. The purpose of the electrode's outer periphery 455 being equal to, or inward from, the cutting edge periphery 460 during rotation is to allow the cutting edges 410 to rotate at high RPMs to engage and cut bone or other hard tissue without the surface or the electrode 425 contacting the targeted tissue.

FIG. 9 further illustrates a method of fabricating the ceramic member 405 with the electrode arrangement 425 carried therein. The molded ceramic member 405 is fabricated with slots 462 that receive the electrode elements 450a-450c, with the electrode elements fabricated from stainless steel, tungsten or a similar conductive material. Each electrode element 450a-450c has a bore 464 extending therethrough for receiving an elongated wire electrode element 465. As can be seen in FIG. 9, and the elongated wire electrode 465 can be inserted from the distal end of the ceramic member 405 through a channel in the ceramic member 405 and through the bores 464 in the electrode elements 450a-450c. The wire electrode 465 can extend through the shaft 412 and is coupled to the RF source 440. The wire electrode element 465 thus can be used as a means of mechanically locking the electrode elements 450a-450c in slots 462 and also as a means to deliver RF energy to the electrode 425.

Another aspect of the invention is illustrated in FIGS. 9-10 wherein it can be seen that the electrode arrangement 425 has a transverse dimension TD relative to axis 115 that is substantial in comparison to the window width W as depicted in FIG. 10. In one variation, the electrode's transverse dimension TD is at least 50% of the window width W, or the transverse dimension TD is at least 80% of the window width W. In the variation of FIGS. 9-10, the electrode transverse dimension TD is 100% or more of the window width W. It has been found that tissue debris and byproducts from RF ablation are better captured and extracted by a window 415 that is wide when compared to the width of the RF plasma ablation being performed.

In general, the tissue resecting system comprises an elongated shaft with a distal tip comprising a ceramic member, a window in the ceramic member connected to an interior channel in the shaft and an electrode arrangement in the ceramic member positioned distal to the window and having a width that is at 50% of the width of the window, at 80% of the width of the window or at 100% of the width of the window. Further, the system includes a negative pressure source 160 in communication with the interior channel 420.

Figure 12A:
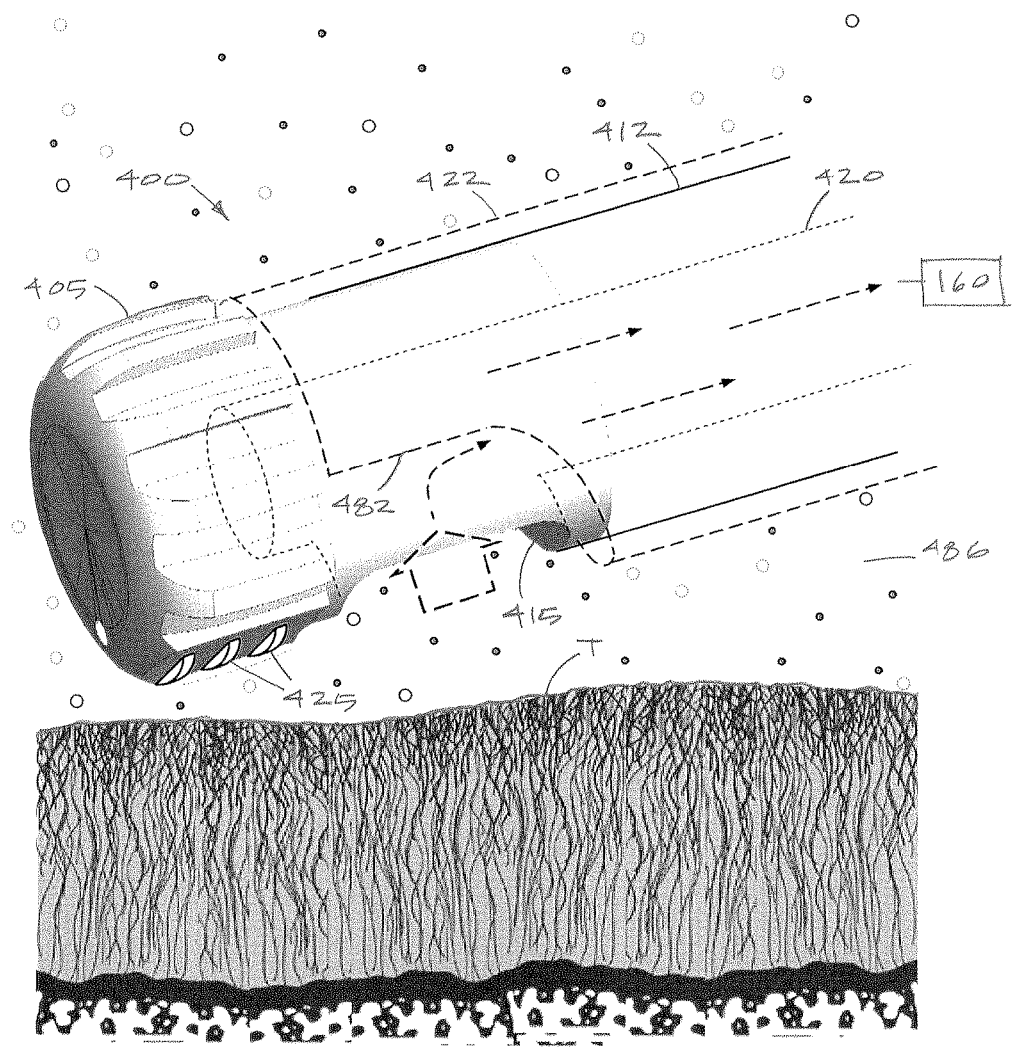
FIG. 12A is a schematic view of the working end and ceramic cutting member of FIGS. 9-11 illustrating a step in a method of use.
Figure 12B:
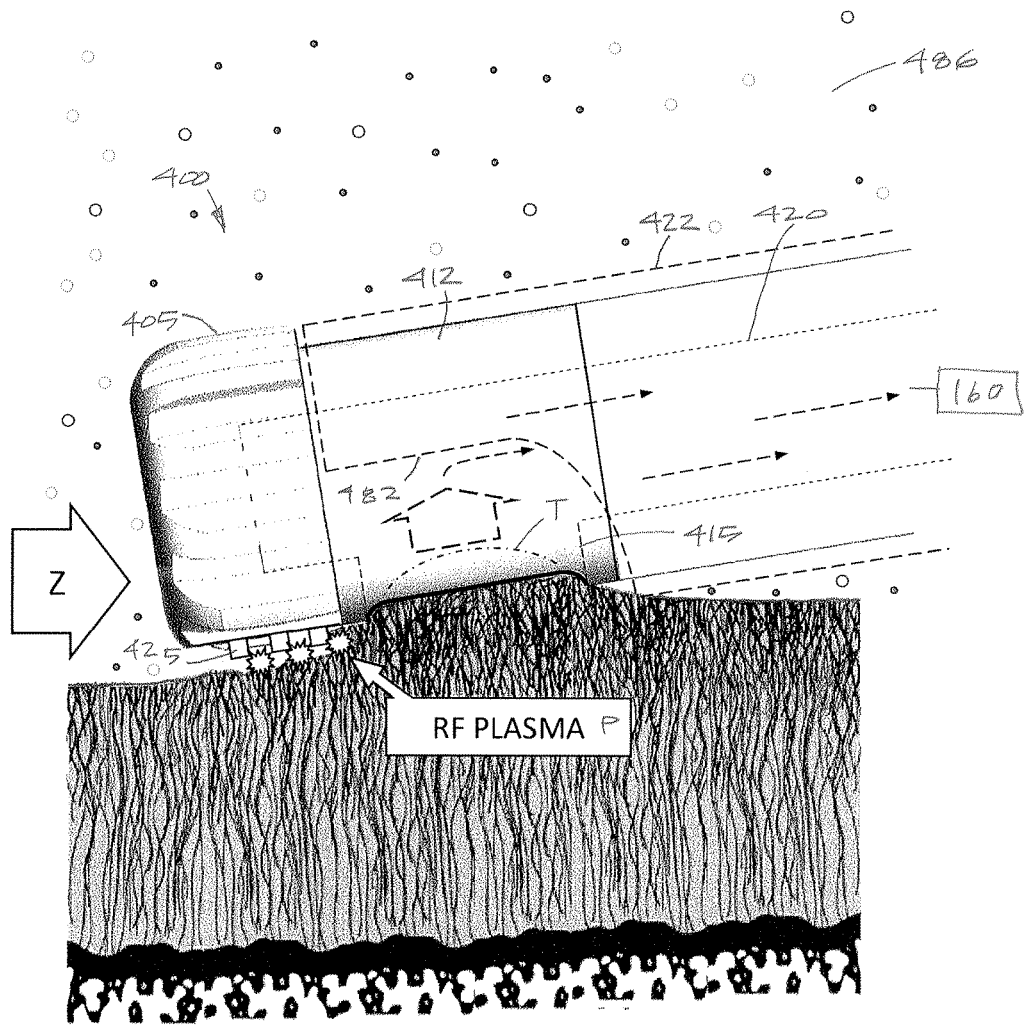
FIG. 12B is another view of the working end of FIG. 12A illustrating a subsequent step in a method of use to ablate a tissue surface.
Figure 12C:
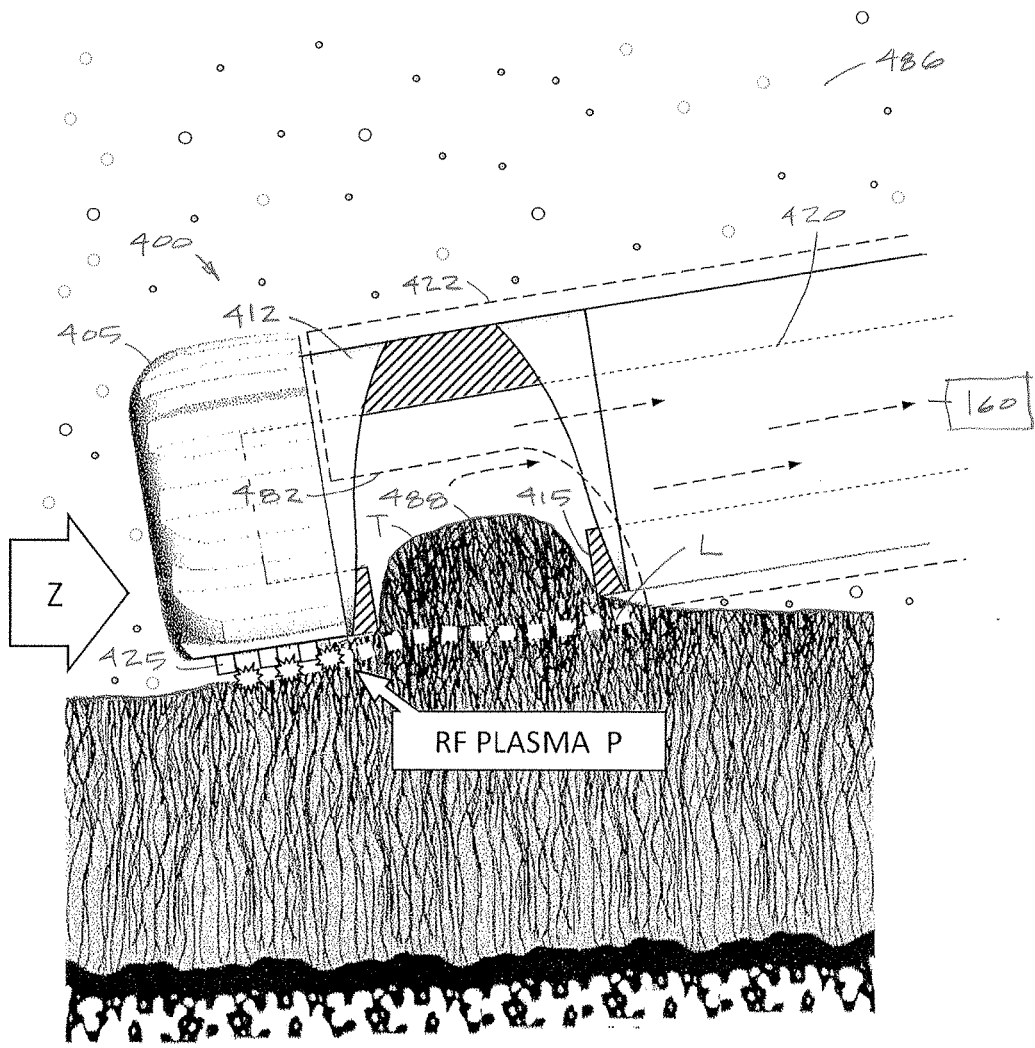
FIG. 12C is a view of the working end of FIG. 12A illustrating a method of tissue resection and aspiration of tissue chips to rapidly remove volumes of tissue.

Now turning to FIGS. 12A-12C, a method of use of the resecting assembly 400 of FIG. 9 can be explained. In FIG. 12A, the system and a controller is operated to stop rotation of the ceramic member 405 in a selected position were the window 415 is exposed in the cut-out 482 of the open end of outer sleeve 422 shown in phantom view. In one variation, a controller algorithm can be adapted to stop the rotation of the ceramic 405 that uses a Hall sensor 484a in the handle 104 (see FIG. 3) that senses the rotation of a magnet 484b carried by inner sleeve hub 140B as shown in FIG. 2. The controller algorithm can receive signals from the Hall sensor which indicated the rotational position of the inner sleeve 412 and ceramic member relative to the outer sleeve 422. The magnet 484b can be positioned in the hub 140B (FIG. 2) so that when sensed by the Hall sensor, the controller algorithm can de-activate the motor drive 105 so as to stop the rotation of the inner sleeve in the selected position.

Under endoscopic vision, referring to FIG. 12B, the physician then can position the electrode arrangement 425 in contact with tissue targeted T for ablation and removal in a working space filled with fluid 486, such as a saline solution which enables RF plasma creation about the electrode. The negative pressure source 160 is activated prior to or contemporaneously with the step of delivering RF energy to electrode 425. Still referring to FIG. 12B, when the ceramic member 405 is positioned in contact with tissue and translated in the direction of arrow Z, the negative pressure source 160 suctions the targeted tissue into the window 415. At the same time, RF energy delivered to electrode arrangement 425 creates a plasma P as is known in the art to thereby ablate tissue. The ablation then will be very close to the window 415 so that tissue debris, fragments, detritus and byproducts will be aspirated along with fluid 486 through the window 415 and outwardly through the interior extraction channel 420 to a collection reservoir. In one method shown schematically in FIG. 12B, a light movement or translation of electrode arrangement 425 over the targeted tissue will ablate a surface layer of the tissue and aspirate away the tissue detritus.

FIG. 12C schematically illustrates a variation of a method which is of particular interest. It has been found if suitable downward pressure on the working end 400 is provided, then axial translation of working end 400 in the direction arrow Z in FIG. 12C, together with suitable negative pressure and the RF energy delivery will cause the plasma P to undercut the targeted tissue along line L that is suctioned into window 415 and then cut and scoop out a tissue chips indicated at 488. In effect, the working end 400 then can function more as a high volume tissue resecting device instead of, or in addition to, its ability to function as a surface ablation tool. In this method, the cutting or scooping of such tissue chips 488 would allow the chips to be entrained in outflows of fluid 486 and aspirated through the extraction channel 420. It has been found that this system with an outer shaft diameter of 7.5 mm, can perform a method of the invention can ablate, resect and remove tissue greater than 15 grams/min, greater than 20 grams/min, and greater than 25 grams/min.

In general, a method corresponding to the invention includes providing an elongated shaft with a working end 400 comprising an active electrode 425 carried adjacent to a window 415 that opens to an interior channel in the shaft which is connected to a negative pressure source, positioning the active electrode and window in contact with targeted tissue in a fluid-filled space, activating the negative pressure source to thereby suction targeted tissue into the window and delivering RF energy to the active electrode to ablate tissue while translating the working end across the targeted tissue. The method further comprises aspirating tissue debris through the interior channel 420. In a method, the working end 400 is translated to remove a surface portion of the targeted tissue. In a variation of the method, the working end 400 is translated to undercut the targeted tissue to thereby remove chips 488 of tissue.

Figure 13A:
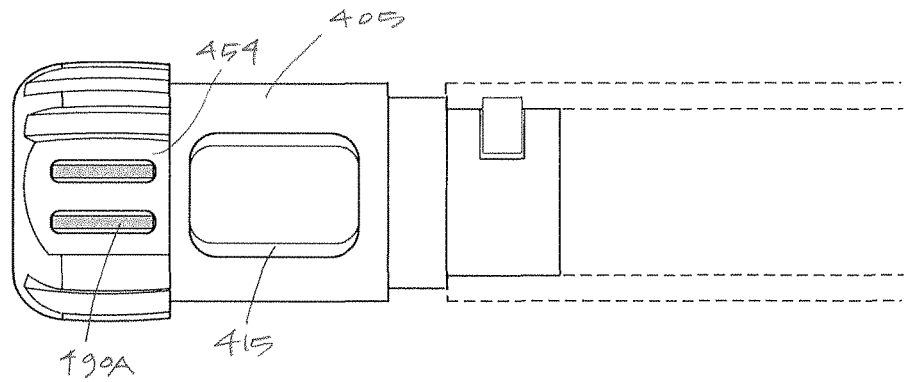
FIG. 13A is an elevational view of an alternative ceramic member and shaft similar to that of FIG. 9 illustrating an electrode variation.
Figure 13B:
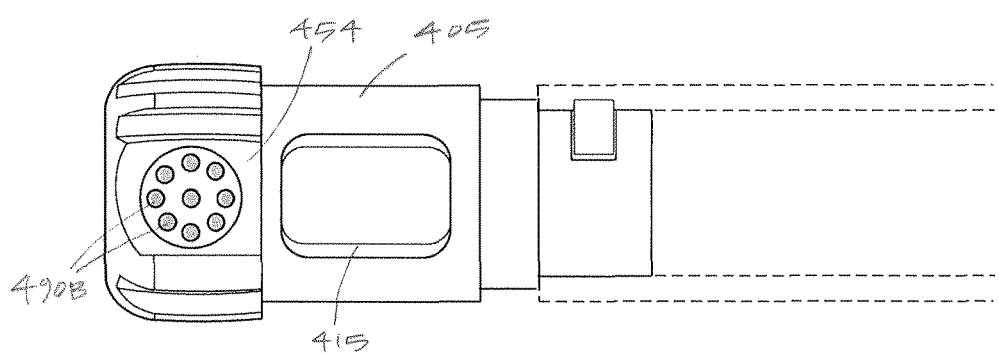
FIG. 13B is an elevational view of another ceramic member similar to that of FIG. 12A illustrating another electrode variation.
Figure 13C:
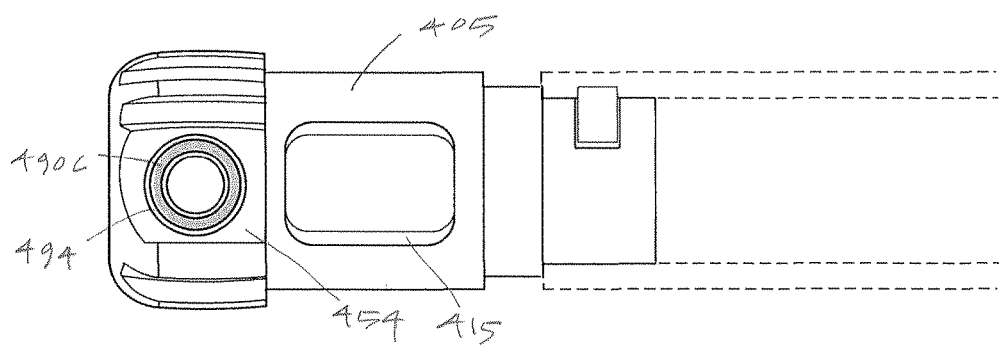
FIG. 13C is an elevational view of another ceramic member similar to that of FIGS. 12A-12B illustrating another electrode variation.

Now turning to FIGS. 13A-13C, other distal ceramic tips of cutting assemblies are illustrated that are similar to that of FIGS. 9-11, except the electrode configurations carried by the ceramic members 405 are varied. In FIG. 13A, the electrode 490A comprises one or more electrode elements extending generally axially distally from the window 415. FIG. 13B illustrates an electrode 490B that comprises a plurality of wire-like elements 492 projecting outwardly from surface 454. FIG. 13C shows electrode 490C that comprises a ring-like element that is partly recessed in a groove 494 in the ceramic body. All of these variations can produce an RF plasma that is effective for surface ablation of tissue, and are positioned adjacent to window 415 to allow aspiration of tissue detritus from the site.

Figure 14:
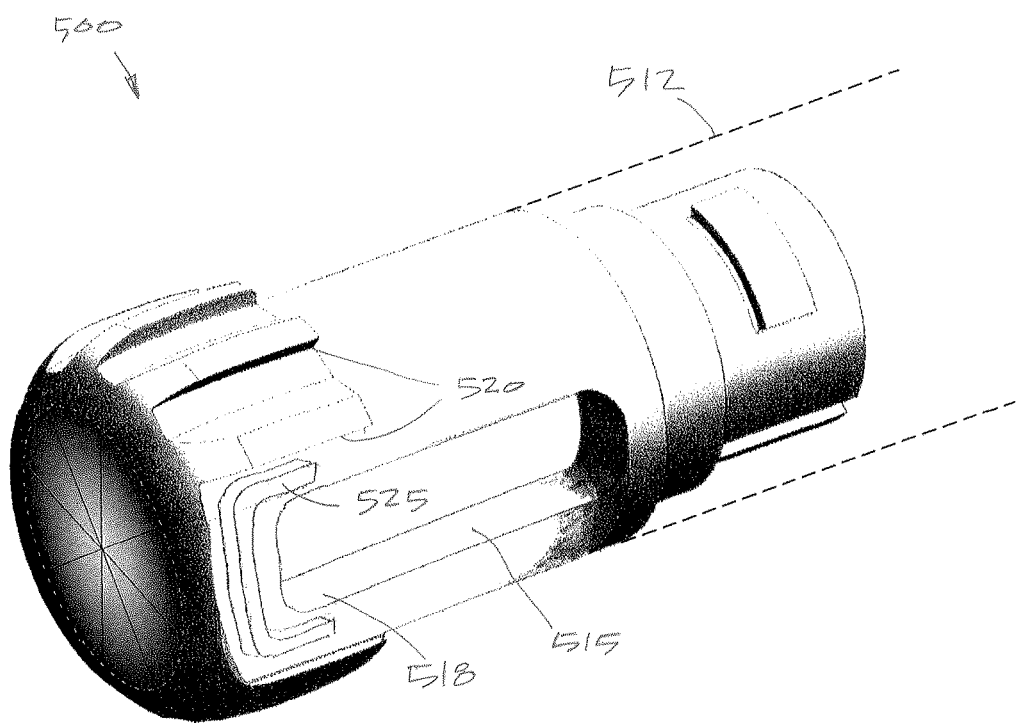
FIG. 14 is a perspective view of an alternative working end and ceramic cutting member with an electrode partly encircling a distal portion of an aspiration window.

FIG. 14 illustrates another variation of a distal ceramic tip 500 of an inner sleeve 512 that is similar to that of FIG. 9 except that the window 515 has a distal portion 518 that extends distally between the cutting edges 520, which is useful for aspirating tissue debris cut by high speed rotation of the cutting edges 520. Further, in the variation of FIG. 14, the electrode 525 encircles a distal portion 518 of window 515 which may be useful for removing tissue debris that is ablated by the electrode when the ceramic tip 500 is not rotated but translated over the targeted tissue as described above in relation to FIG. 12B. In another variation, a distal tip 500 as shown in FIG. 14 can be energized for RF ablation at the same time that the motor drive rotates back and forth (or oscillates) the ceramic member 500 in a radial arc ranging from 1° to 180° and more often from 10° to 90°.

Figure 15A:
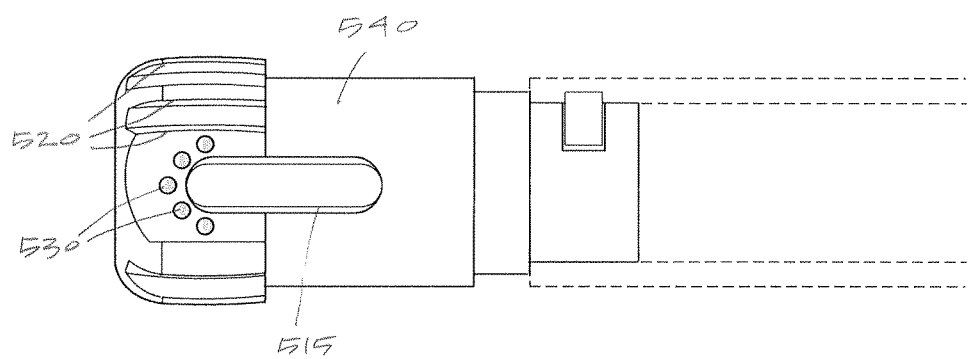
FIG. 15A is an elevational view of a working end variation with an electrode arrangement partly encircling a distal end of the aspiration window.
Figure 15B:
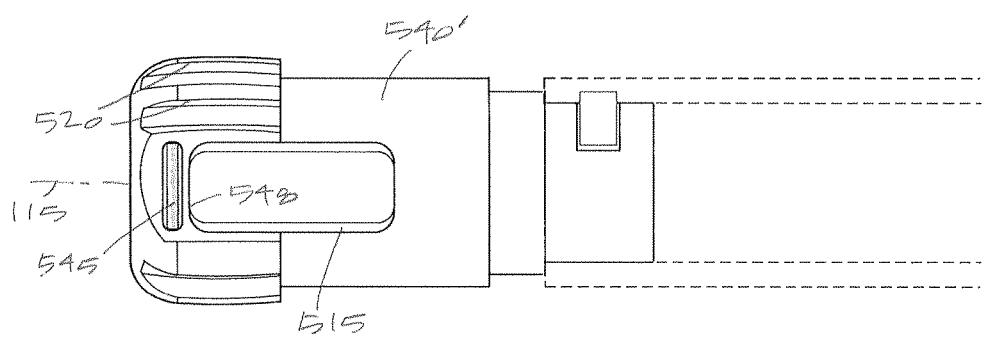
FIG. 15B is an elevational view of another working end variation with an electrode positioned adjacent a distal end of the aspiration window.

FIGS. 15A-15B illustrate other distal ceramic tips 540 and 540' that are similar to that of FIG. 14 except the electrode configurations differ. In FIG. 15A, the window 515 has a distal portion 518 that again extends distally between the cutting edges 520, with electrode 530 comprising a plurality of projecting electrode elements that extend partly around the window 515. FIG. 15B shows a ceramic tip 540' with window 515 having a distal portion 518 that again extends distally between the cutting edges 520. In this variation, the electrode 545 comprises a single blade element that extends transverse to axis 115 and is in close proximity to the distal end 548 of window 515.

Figure 16:
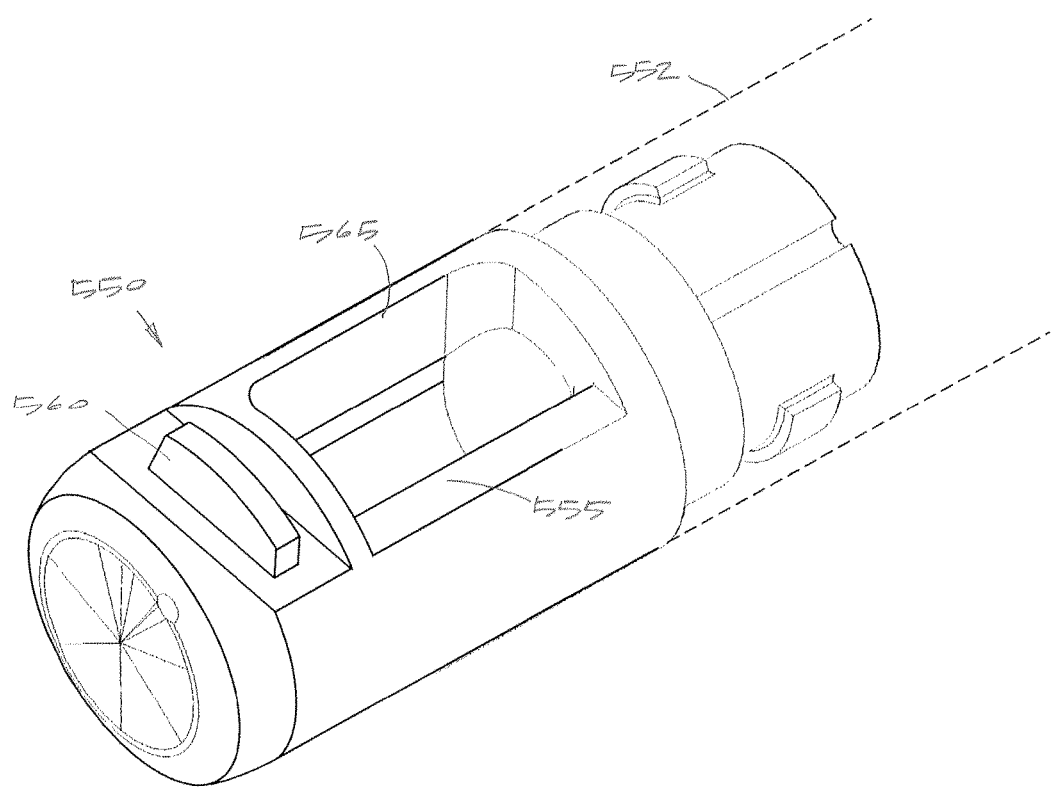
FIG. 16 is a perspective view of a variation of a working end and ceramic member with an electrode adjacent a distal end of an aspiration window having a sharp lateral edge for cutting tissue.

FIG. 16 illustrates another variation of distal ceramic tip 550 of an inner sleeve 552 that is configured without the sharp cutting edges 410 of the embodiment of FIGS. 9-11. In other respects, the arrangement of the window 555 and the electrode 560 is the same as described previously. Further, the outer periphery of the electrode is similar to the outward surface of the ceramic tip 550. In the variation of FIG. 16, the window 555 has at least one sharp edge 565 for cutting soft tissue when the assembly is rotated at a suitable speed from 500 to 5,000 RPM. When the ceramic tip member 550 is maintained in a stationary position and translated over targeted tissue, the electrode 560 can be used to ablate surface layers of tissue as described above.

Figure 17:
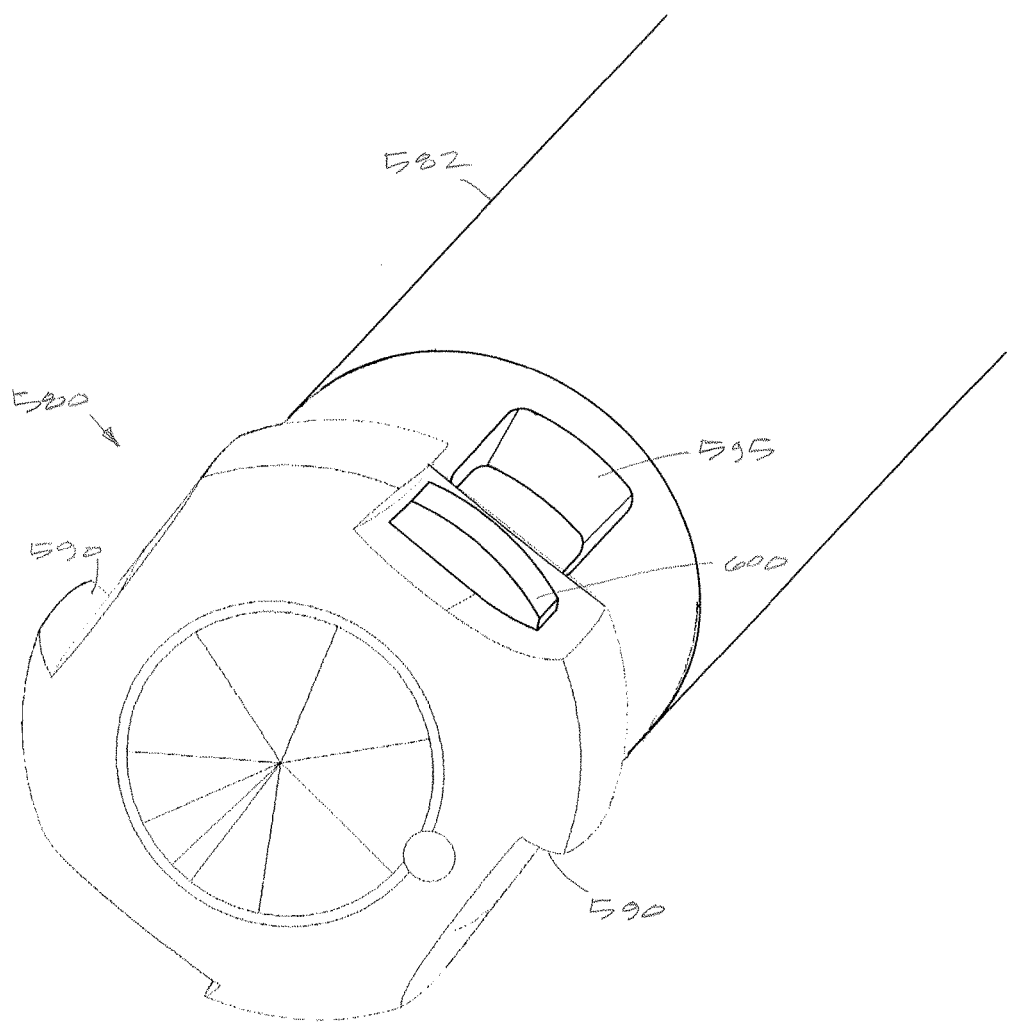
FIG. 17 is a perspective view of a variation of a working end and ceramic member with four cutting edges and an electrode adjacent a distal end of an aspiration window.

FIG. 17 depicts another variation of distal ceramic tip 580 coupled to an inner sleeve 582 that again has sharp burr edges or cutting edges 590 as in the embodiment of FIGS. 9-11. In this variation, the ceramic monolith has only 4 sharp edges 590 which has been found to work well for cutting bone at high RPMs, for example from 8,000 RPM to 20,000 RPM. In this variation, the arrangement of window 595 and electrode 600 is the same as described previously. Again, the outer periphery of electrode 595 is similar to the outward surface of the cutting edges 590.

Figure 21A:
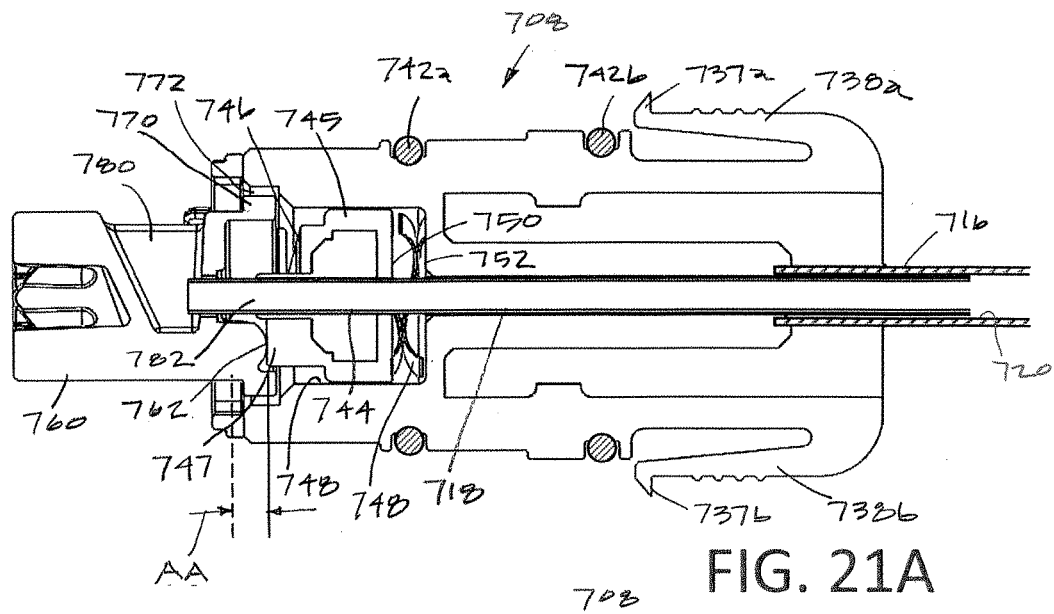
FIG. 21A is a sectional view of the hub of the probe of FIG. 18 taken along line 21A-21A of FIG. 18 showing an actuation mechanism in a first position.
Figure 21B:
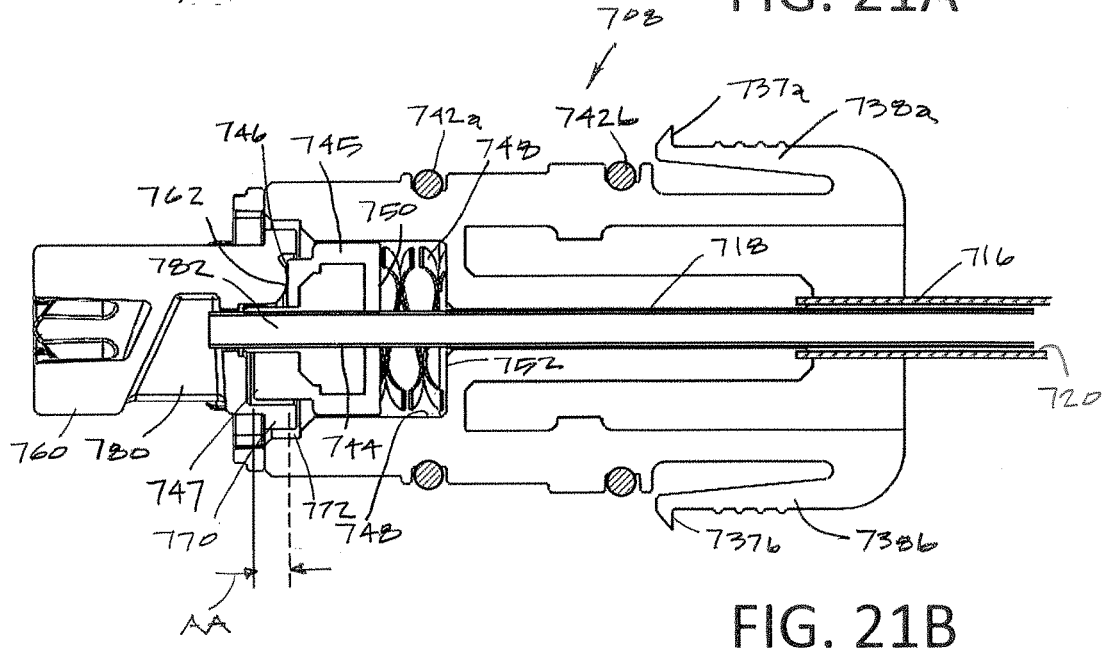
FIG. 21B is a sectional view of the hub of FIG. 21A showing the actuation mechanism in a second position.
Figure 22:
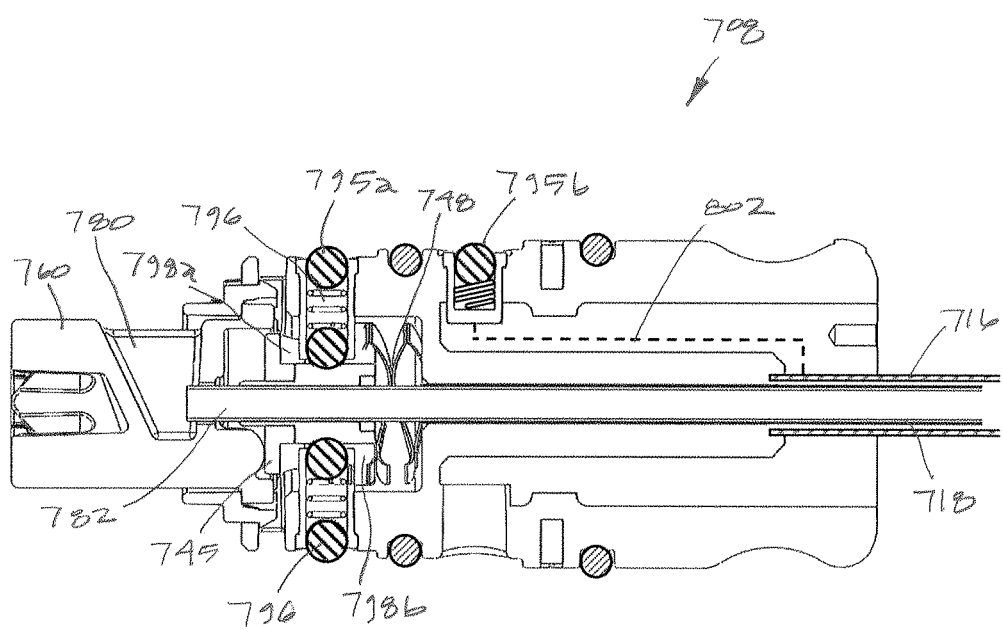
FIG. 22 is a sectional view of the hub of FIG. 21A rotated 90° to illustrate electrical contacts and pathways in the hub.
Figure 23:
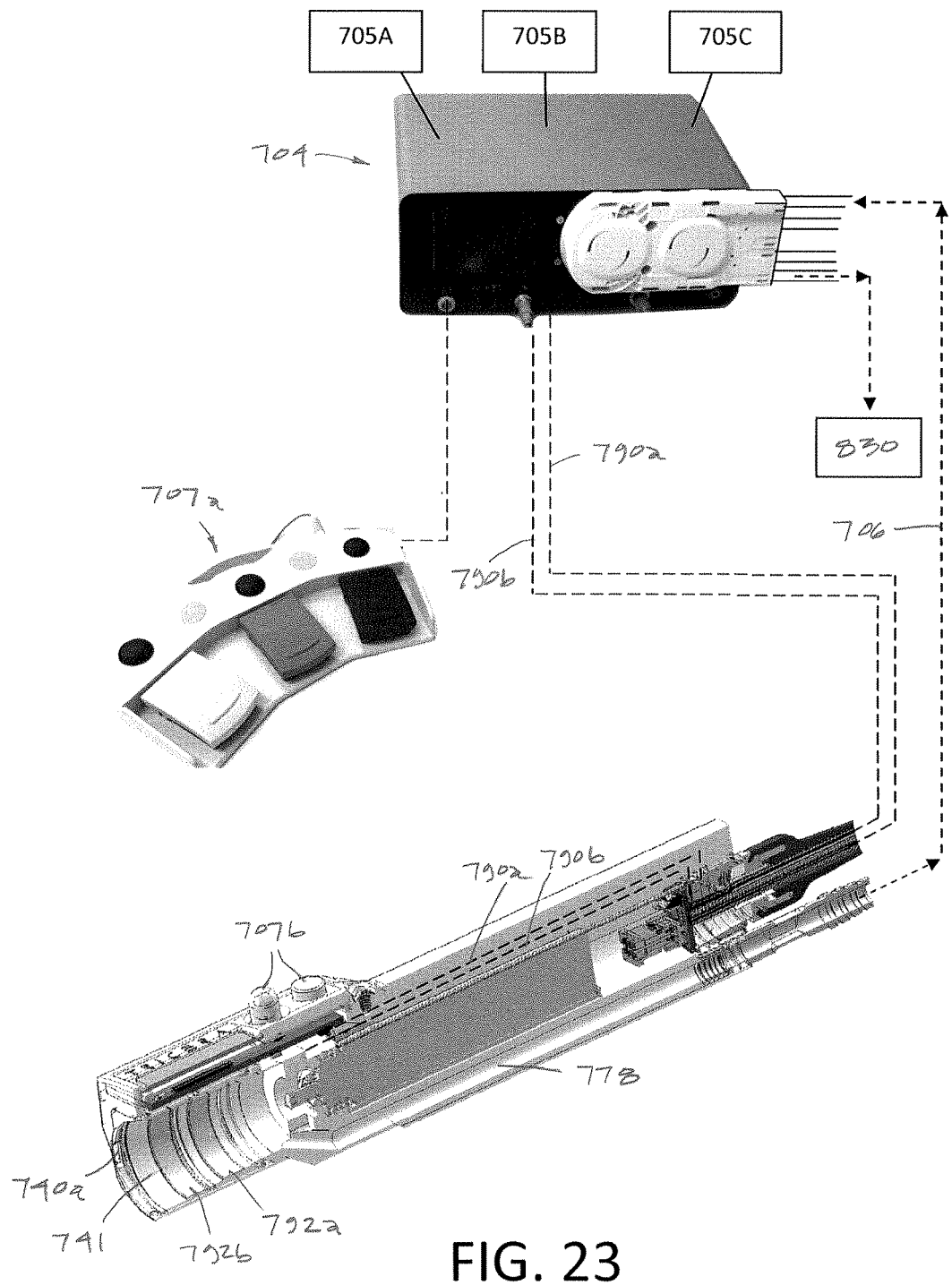
FIG. 23 is a schematic diagram of as RF system that includes a controller console, handpiece with a motor drive and a footswitch.

FIGS. 18-24 illustrate another electrosurgical RF ablation device or probe 700 (FIG. 18) that is adapted for use with a handpiece 702 and motor drive unit 105 (see FIG. 23). In FIG. 23, the console 704 carries RF source 705A and a negative pressure source 705B which can comprise a peristaltic pump and cassette to provide suction though tubing 706 coupled to the handpiece 702 as is known in the art. The console 704 further can carry a controller 705C that operates the motor drive as well as actuation and/or modulation of the RF source 705A and negative pressure source 705B. A footswitch 707a is provided for operation of RF source 705A, negative pressure source 705B and optionally the motor drive. In addition, the motor drive 105, RF source and negative pressure source can be operated by control buttons 707b in the handpiece 702 (FIG. 23). In the RF probe of FIGS. 18 to 22, the motor drive 105 does not rotate a cutting blade or electrode but instead moves or reciprocates an RF electrode axially at a selected reciprocation rate (which may be a high or low reciprocation rate or a single reciprocation) to dynamically ablate, resect and remove tissue.

Figure 18:
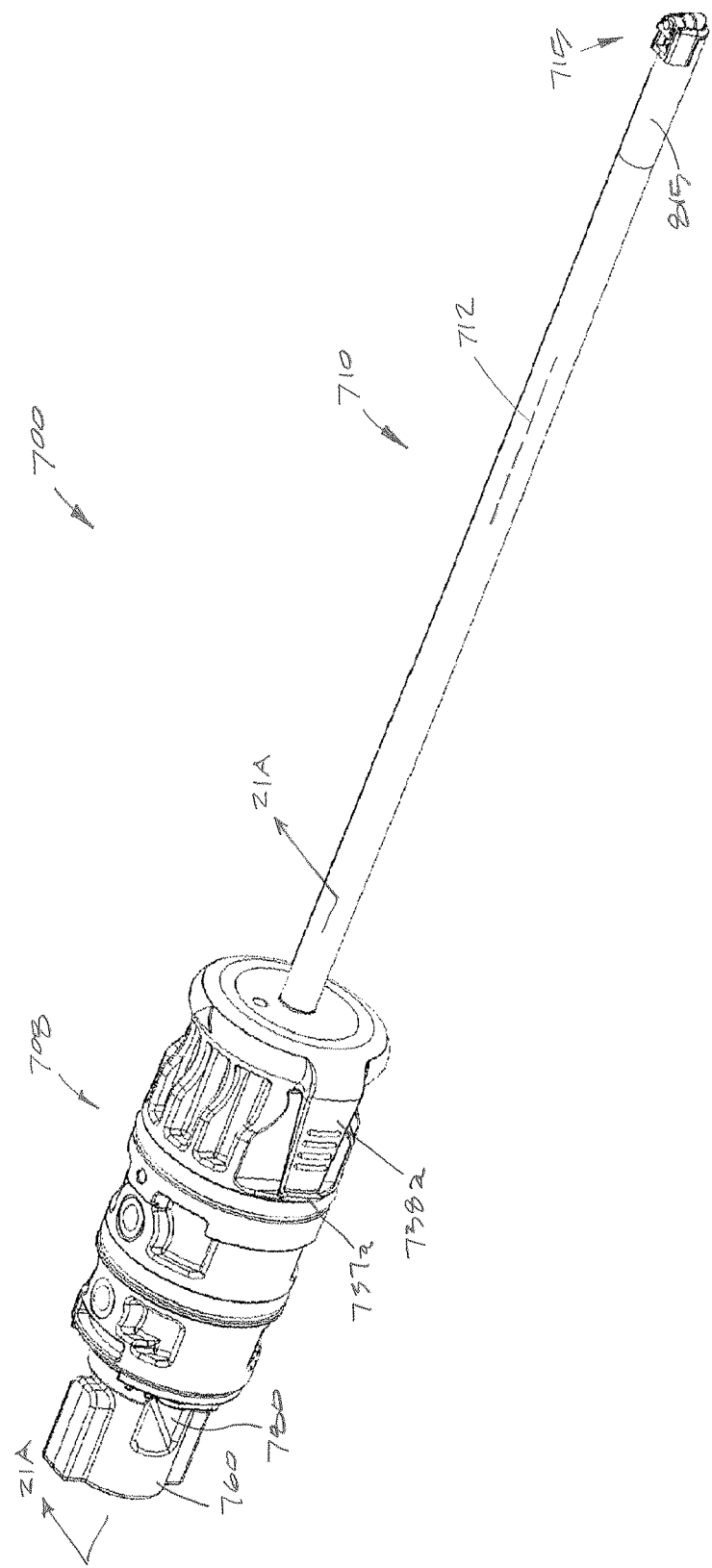
FIG. 18 is a perspective view of a variation of another type of electrosurgical ablation device that can be detachably coupled to a handpiece as shown in FIG. 23.

More in particular, referring to FIG. 18, the detachable RF ablation probe 700 has a proximal housing portion or hub 708 that is coupled to an elongated shaft or extension portion 710 that has an outer diameter ranging from about 2 mm to 7 mm, and in one variation is from 5 mm to 6 mm in diameter. The shaft 710 extends about longitudinal axis 712 to a working end housing or body 715 that comprises a dielectric material such as a ceramic as described above. Referring to FIGS. 18, 19A-19B and 20A-20B, it can be seen that elongated shaft 710 comprises an outer sleeve 716 and an inner sleeve 718. Both sleeves 716 and 718 can be a thin wall stainless steel tube or another similar material or composite that is electrically conductive. The outer sleeve 716 has a distal end 719 that is coupled to the ceramic housing 715 and an interior channel 720 extending through the housing 715 to a distal channel opening 722 in housing 715. In this variation, the channel opening 722 in part faces sideways or laterally in the housing 715 relative to axis 712 and also faces in the distal direction.

Figure 19A:
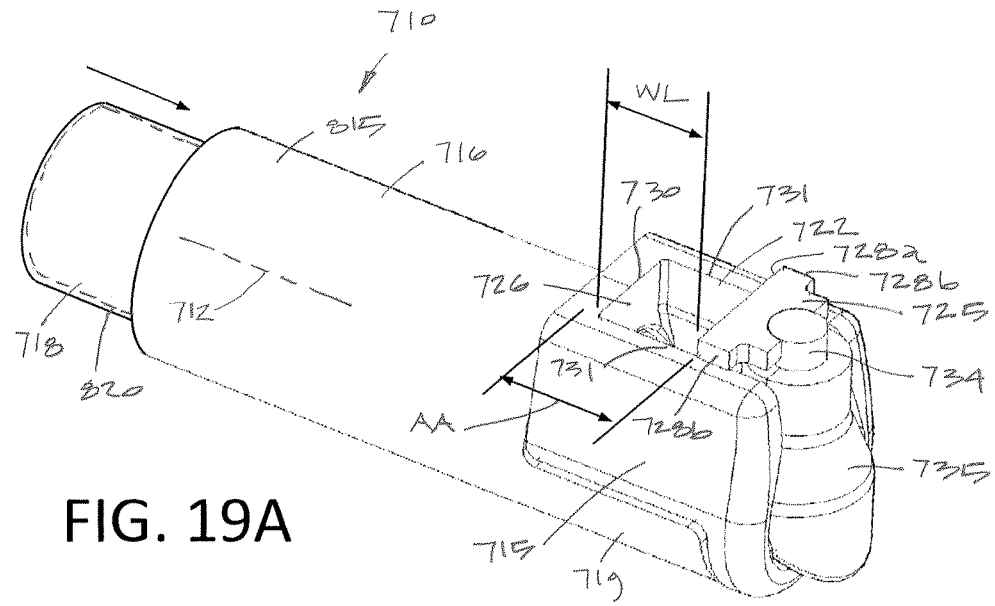
FIG. 19A is a perspective view of the working end and ceramic housing of the device of FIG. 18 showing an electrode in a first position relative to a side-facing window.
Figure 19B:
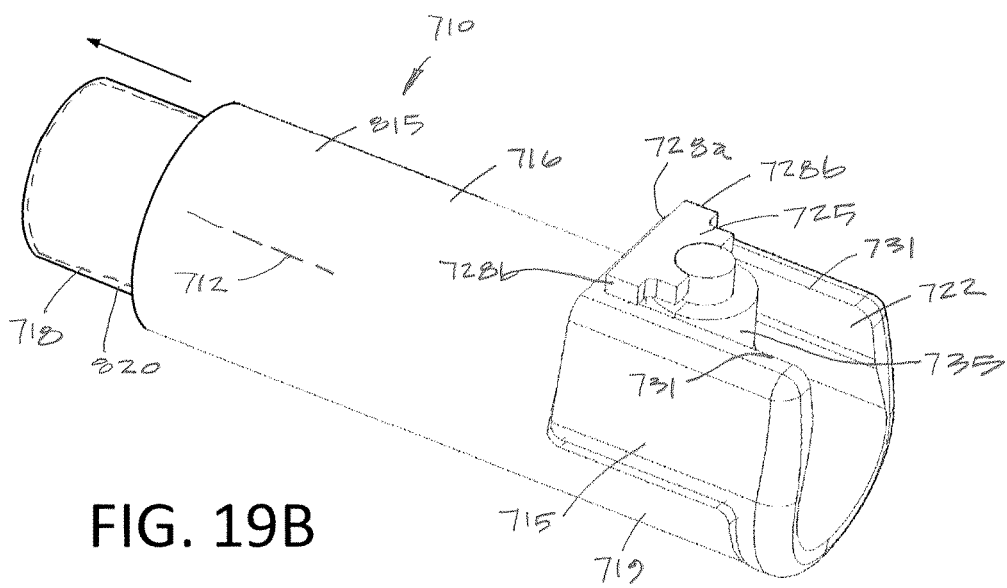
FIG. 19B is a perspective view of the working end of FIG. 19A showing the electrode in a second position relative to the window.
Figure 20A:
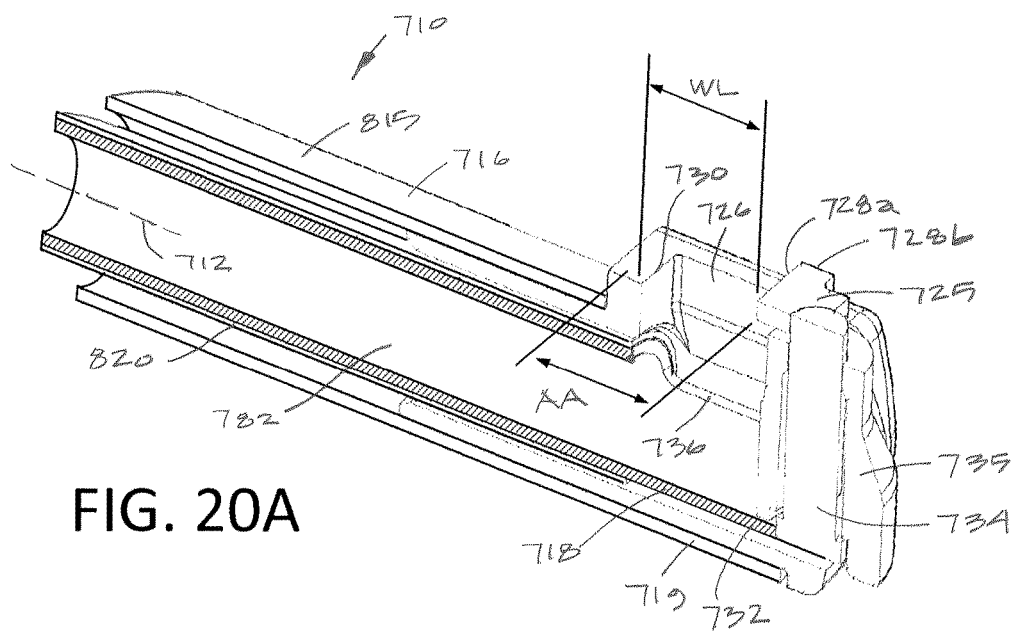
FIG. 20A is a sectional view of the working end and electrode of FIG. 19A.
Figure 20B:
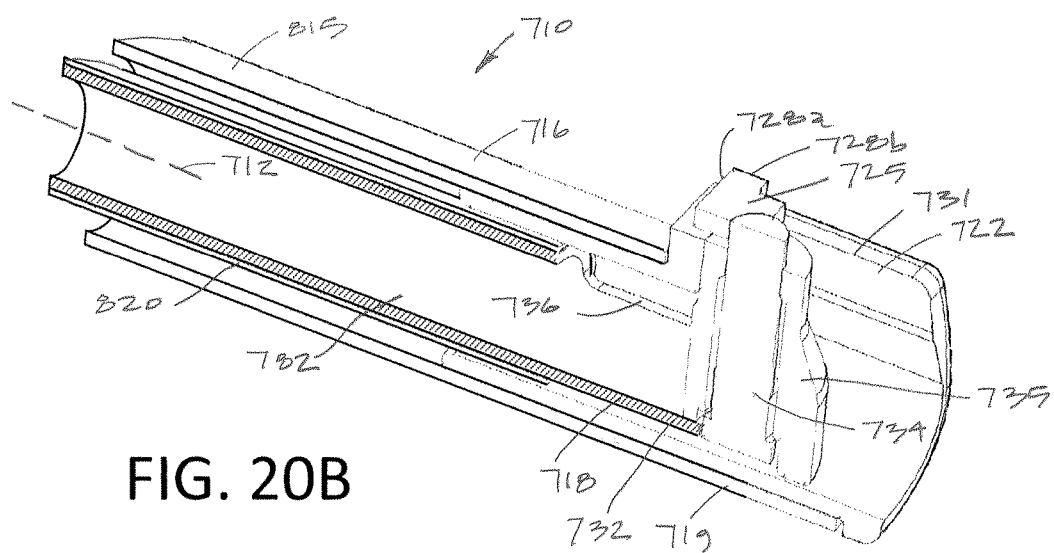
FIG. 20B is a sectional view of the working end and electrode of FIG. 19B.

Referring to FIGS. 19A-19B, a moveable active electrode 725 is configured to extend laterally across a window 726 which has a planar surface and is a section of opening 722 in housing 715. As can be seen in FIGS. 20A-20B, the electrode 725 is carried at the distal end of reciprocating inner sleeve 718. The electrode 725 is adapted to be driven by motor drive unit 105 in handpiece 702 (see FIG. 23) so that proximal-facing edge 728a and side-facing edges 728b of electrode 725 move axially relative to the window 726. FIG. 19A and the corresponding sectional view of FIG. 20A show the inner sleeve 718 and electrode 725 moved by motor drive 105 to an extended or distal axial position relative to window 726. FIGS. 19B and 20B show the inner sleeve 718 and electrode 725 moved by the motor drive to a non-extended or retracted position relative to window 726. In FIGS. 19A and 20A, the window 726 has an open window length WL that can be defined as the dimension between the proximal window edge 730 and the proximal-facing electrode edge 728. The stroke AA of the moving electrode 725 is also shown in FIGS. 19A-20B wherein the electrode edge 728a in the retracted position (FIGS. 19B and 20B) is adapted to extend over the proximal window edge 730 to shear tissue and clean the electrode surface. Likewise, referring to FIGS. 19A-19B, the side-facing edges 728b of electrode 725 extend over the lateral edges 731 of window 726 to shear tissue engaged by suction in the window.

As can be seen in FIGS. 20A-20B, the inner sleeve 718 comprises a thin-wall tube of stainless steel or another conductive material, and is coupled to RF source 705A (FIG. 23) to carry RF current to the electrode 725. The inner sleeve 718 has a distal end 732 that coupled by a weld to a conductive metal rod or element 734 that extends transversely through a dielectric body 735 carried by the inner sleeve. The conductive element 734 is welded to electrode 725 that extends laterally across the window 726. The dielectric body 735 can be a ceramic, polymer or combination thereof and is in part configured to provide an insulator layer around to electrical conductive components (inner sleeve 718 and transverse rod 734) to define the "active electrode" as the limited surface area of electrode 725 which enhances RF energy delivery to the electrode edges 728a and 728b for tissue cutting. The inner sleeve 718 also has side-facing window 736 therein that cooperates with window 726 in housing 715 to provide suction through the windows 736 and 726 from negative pressure source 705B (see FIGS. 20A and 23) to draw tissue into the window 726.

Now turning to FIGS. 18, 21A-21B, 22 and 23, the mechanism that axially translates the electrode 725 in window 726 is described in more detail. As can be understood from FIGS. 18, 21A and 23, the RF ablation probe 700 can be locked into handpiece 702 of FIG. 22 by inserting tabs 737a and 737b on flex arms 738a and 738b (FIGS. 18 and 21A) into receiving openings 740a and 740b in handpiece 702 (FIG. 23). O-rings 742a and 742b are provided in hub 708 (FIG. 21A-21B) to seal the hub 708 into the receiving channel 741 in the handpiece 702 (FIG. 23).

Referring now to FIGS. 21A-21B, the hub 708 is fixed to outer sleeve 716 that has a bore or channel 720 therein in which the inner sleeve 718 is slidably disposed. A proximal end 744 of inner sleeve 718 has an actuator collar 745 of an electrically conductive material attached thereto with a proximal-facing surface 746 that has a bump or cam surface 747 thereon. The actuator collar 745 is adapted to reciprocate within bore 748 in the hub 708. FIG. 21A shows the actuator collar 745 in an extended position which corresponds to the extended electrode position of FIGS. 19A and 20A. FIG. 21B shows the actuator collar 745 in a non-extended or retracted position which corresponds to the retracted electrode position of FIGS. 19B and 20B.

The actuator collar 745 and hub 708 include slot and key features described further below to allow for axial reciprocation of the sliding actuator collar 745 and inner sleeve 718 while preventing rotation of the collar 745 and sleeve 718. A spring 748 between a distal surface 750 of actuator collar 745 and a proximally facing internal surface 752 of hub 708 urges the sliding actuator collar 745 and the moveable active electrode 725 toward the retracted or proximal-most position as shown in FIGS. 19B, 20B and 21B.

The motor drive 105 of handpiece 702 (FIG. 23) couples to a rotating drive coupling 760 fabricated of a non-conductive material that rotates in hub 708 as shown in FIGS. 18 and 21A-21B. The drive coupling 760 has a distal cam surface 762 that engages the proximal-facing cam surface 747 on the actuator collar 745 so that rotation of drive coupling 760 will reciprocate the sliding actuator collar 745 through a forward and backward stroke AA, as schematically shown in FIGS. 21A-21B. While the cam surfaces 762 and 747 are illustrated schematically as bumps or cams, one of skill in the art will appreciate that the surfaces can be undulating or "wavy" or alternately comprise multiple facets to provide a ratchet-like mechanism wherein rotation of the rotating drive coupling in 360° will reciprocate the sliding actuator collar 745 through a selected length stroke multiple times, for example from 1 to 100 times per rotation of the drive coupling 760. It should also be appreciated that while full and continuous rotation of the rotating coupling 760 will usually be preferred, it would also be possible to rotationally oscillate (periodically reverse the direction of rotation between clockwise and counter-clockwise) the rotating drive coupling 760, for example to control a length of travel of the moveable active electrode 725 in the window 726 where a rotation of less than 360° will result in a shortened length of travel. The stroke of the sliding actuator collar 745 and electrode 725 can be between 0.01 mm and 10 mm, and in one variation is between 0.10 mm and 5 mm. The selected RPM of the motor determines the reciprocation rate, and in one variation a controller 705C can select a motor operating RPM to provide a reciprocation rate between 1 Hz and 1,000 Hz, usually between 1 Hz and 500 Hz. In another variation, the RF ablation probe 700 can be selectively operated in different reciprocation modes (by controller 705C) to provide different reciprocation rates to provide different RF effects when treating tissue. In an additional variation, the length of the electrode stroke can be selected for different modes, wherein the housing 708 can be provided with a slidable adjustment (not shown) to adjust the distance between the cam surfaces 747 and 762 of the sliding collar 745 and rotating coupling 760, respectively.

The RF probe of FIGS. 18-22 also can be operated in different RF modes. As described above, a typical RF mode for dynamic RF ablation reciprocates the electrode 725 at a selected high speed while delivering RF current in a cutting waveform to thereby create a plasma that ablates tissue. In another RF mode, the controller 705C can include an algorithm that stops the reciprocation of electrode 725 in the extended position of FIGS. 19A and 20A and then RF RF current in a coagulation waveform can be delivered to the electrode 725. The operator can then move the stationary electrode over a targeted site for coagulation of tissue. In yet another RF mode, the controller 705C can reciprocate the electrode 725 as at slow rate (e.g., 1 Hz to 500 Hz) while delivering a coagulation waveform to coagulate tissue.

Figure 24:
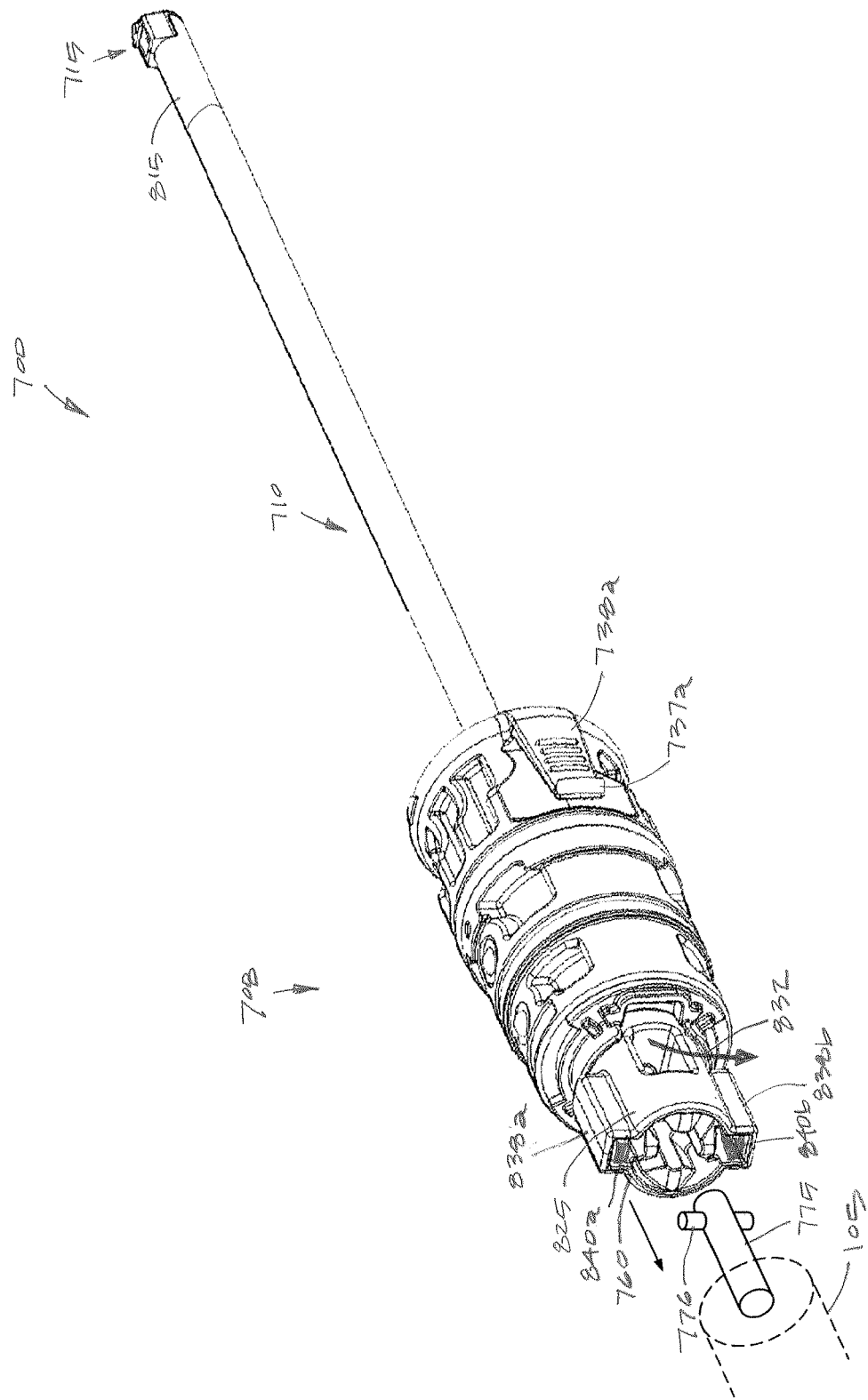
FIG. 24 is a perspective view of the RF probe of FIG. 18 from a different angle showing the drive coupling.

Referring to FIGS. 18, 21A-21B and 24, the rotating coupling 760 is rotationally maintained in hub 708 by a flange 770 that projects into annular groove 772 in the hub 708. The rotating drive coupling 760 is configured for coupling with the drive shaft 775 and transverse pin 776 of motor drive unit 105 as shown in FIG. 24. As in previous embodiments of cutting or shaver assemblies, the negative pressure source 705B is coupled to a passageway 778 in handpiece 702 (FIG. 23) that further communicates through the interior of the handpiece with opening 780 in the drive coupling 760 (see FIGS. 21A-21B) and lumen 782 in inner sleeve 718 to suction tissue into window 726, as can be understood from FIGS. 19A-21B.

FIG. 22 is a longitudinal sectional view of the device hub 708 rotated 90° from the sectional views of FIGS. 21A-21B. FIG. 22 shows the means provided for connecting the RF source 705A to the probe 700 and electrodes. In FIG. 23, first and second electrical leads 790a and 790b are shown schematically extending from RF source 705A through handpiece 702 to electrical contact surfaces 792a and 792b in the receiving channel 741 in the handpiece 702. FIG. 22 shows electrical contacts 795a and 795b in hub 708 as described previously which engage the contact surfaces 792a and 792b in the handpiece. In FIG. 22, the first electrical lead 790a and contact surface 792a delivers RF electrical current to contact 795a in hub 708 which provides at least one ball and spring contact assembly 796 to deliver current to the conductive actuator collar 745 and inner sleeve 718 which is connected to active electrode 725 as described above. It can be understood that the ball and spring contact assembly 796 will allow the actuator collar 745 to reciprocate while engaging the contact assembly 796. In one variation, two ball and spring contact assemblies 796 are provided on opposing sides of the hub 708 for assuring RF current delivery to the actuator collar 745. The inward portions of the two ball and spring contact assemblies 796 also are disposed in axial channels or slots 798a and 798b in the actuator collar 745 and thus function as a slot and key features to allow the actuator collar 745 to reciprocate but not rotate.

Referring again to FIG. 22, the second electrical lead 790b connects to contact surface 792b in handpiece receiving channel 741 which engages the electrical contact 795b in hub 708 of the RF probe 700. It can be seen that an electrical path 802 extends from electrical contact 795b in the hub 708 to outer sleeve 716 wherein and an exposed portion of the outer sleeve 716 comprises a return electrode 815 as shown in FIGS. 18, 19A-19B and 24. It should be appreciated that the outer sleeve 716 can be covered on the inside and outside with a thin electrically insulating cover or coating (not shown) except for the exposed portion which comprises the return electrode 815. The inner sleeve 718 has an insulative exterior layer 820 such as a heat shrink polymer shown in FIGS. 19A-19B and 20A-20B. The insulative exterior layer 820 on the inner sleeve 718 is provided to electrically insulate the inner sleeve 718 from the outer sleeve 716.

In a method of operation, it can be understood that the device can be introduced into a patient's joint that is distended with saline solution together with an endoscope for viewing the working space. Under endoscopic vision, the device working end is oriented to place the electrode 725 against a targeted tissue surface in the patient's joint, and thereafter the RF source 705A and negative pressure source 705B can be actuated contemporaneously to thereby suction tissue into the window 726 at the same time that an RF plasma is formed about the reciprocating electrode 725 which then ablates tissue. The ablated tissue debris is suctioned through the windows 726 and 736 into lumen 782 of inner sleeve 718 to the fluid outflow pathway in the handpiece 702. Ultimately, the tissue debris is carried though the outflow pump system to the collection reservoir 830 (FIG. 23). The device and system can be actuated by the footswitch 707a or a button 707b in the control panel of the handpiece 702 as described previously.

FIG. 24 shows the RF ablation probe or assembly 700 from a different angle where it can be seen that the rotating drive coupling 760 has a bore 822 and at least one slot 824 therein to receive that motor drive shaft 775 and transverse pin 776. In another aspect of the invention, the drive coupling 760 has a smooth exterior surface 825 in 360° around the coupling to provide an enclosure that surrounds and enclosed shaft 775 and transverse pin 776. The exterior surface 825 and 360° enclosure is configured to prevent a fluid outflow indicated by arrow 832 (which carries resected tissue debris) from clogging the system. It can be understood that resected tissue may include elongated, sinewy tissue strips that can wrap around the drive coupling 760 which is spinning at 5,000-15,000 RPM after being suctioned with fluid through opening 780 in the drive coupling 760. Prior art devices typically have a drive shaft and pin arrangement that is exposed which then is susceptible to "catching" tissue debris that may wrap around the coupling and eventually clog the flow pathway. For this reason, the rotating drive coupling 760 has a continuous, smooth exterior surface 825. In an aspect of the present invention, a disposable arthroscopic cutting or ablation device is provided that includes a rotating drive coupling that is adapted to couple to a motor drive shaft in a handpiece, wherein the rotating drive coupling has a continuous 360° enclosing surface that encloses the drive shaft and shaft-engaging features of the drive coupling. In other words, the drive coupling 760 of the invention has motor shaft-engaging features that are within an interior receiving channel of the drive coupling. In another aspect of the invention, referring to FIG. 24, the drive collar 760 of a shaver blade includes enclosing features 838a and 838b that are configured to carry magnets 840a and 840b. Such magnets are adapted to cooperate with Hall sensors (not shown) in the handpiece 702. Such Hall sensors can be used for one or more purposes, including (i) calculating shaft RPM, (ii) stopping shaft rotation and thus electrode 725 and the inner sleeve window 736 in a selected axial position, and (iii) identifying the type of shaver blade out of a potential catalog of different shaver blades wherein the controller that operates the RF source 705A, negative pressure source 705B and motor controller 705C then can select different operating parameters for different shaver blades based identifying the blade type.

Figure 25:
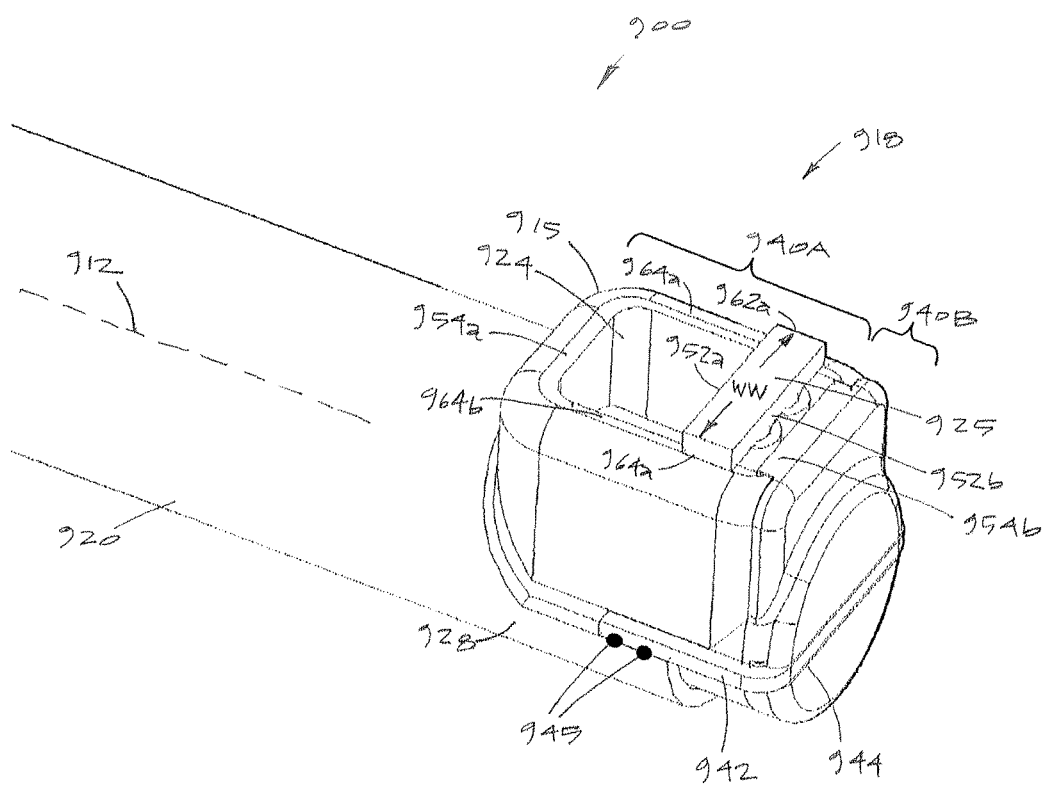
FIG. 25 is a perspective view of the working end and electrode of a variation of an RF probe similar to that of FIGS. 19A-19B.
Figure 26:
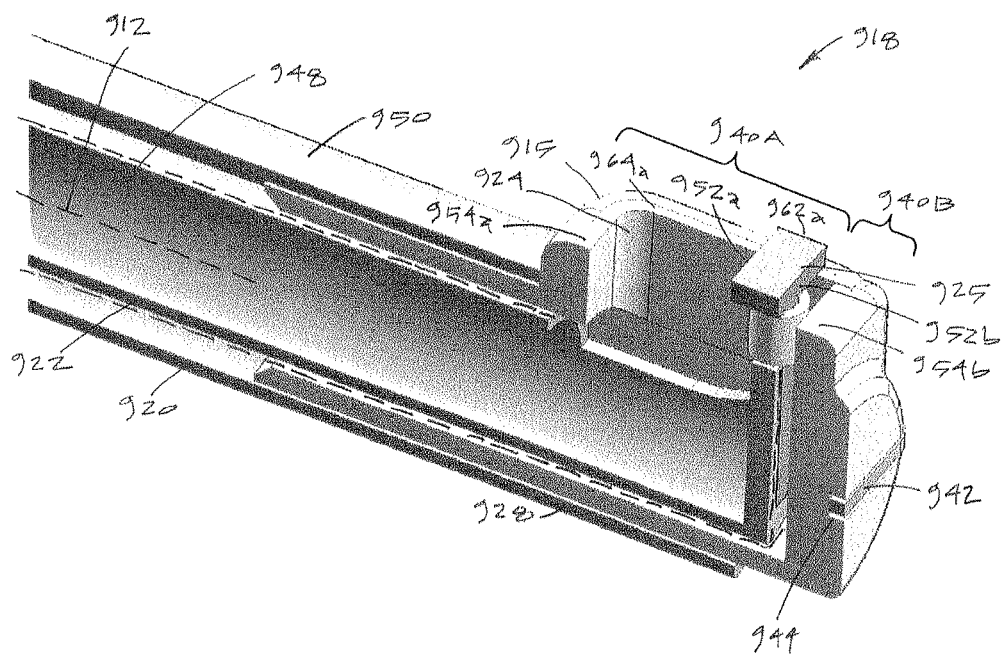
FIG. 26 is a sectional view of working end of FIG. 25 showing the electrode edges that are adapted to shear tissue.

FIGS. 25-26 illustrate a variation of an RF probe 900 with a working end 918 that is similar to the version of FIGS. 18-24. The electrosurgical RF ablation probe or assembly 900 again is adapted for use with the handle 702 and motor drive unit 105 as shown in FIG. 23.

Referring to FIGS. 25-26, the working end 918 includes a ceramic housing 915 that has a lateral or side-facing window 924 in which the active electrode 925 reciprocates at high speed as described previously. The ceramic housing 915 is coupled to the distal end 928 of outer sleeve 920. As can be seen in FIGS. 25-26, the ceramic housing 915 is formed in a proximal body portion 940A and a distal end-cap 940B which allows for simplified assembly of the working end 918. The distal end-cap 940B is held in place by metal retaining strap 942 that fits into notch 944 in the end-cap 940B and is welded at several points 945 to the distal end 928 of outer sleeve 920 (FIG. 25).

The inner sleeve 922 can be covered with an insulative shrink tube 948 as the inner sleeve carries electrical current to the active electrode 925 (FIG. 26). The exterior of outer sleeve 920 comprises the return electrode 950. In this variation, the proximal and distal edges 952a-952b of the electrode are adapted to extend slightly over the window edges 954a-954b so as to shear tissue with the energized RF electrode 925. Likewise, the lateral edges 962a-962b of electrode 925 are adapted to extend over the lateral window edges 964a-964b to insure tissue suctioned into the window is entirely cut or sheared.

Figure 27:
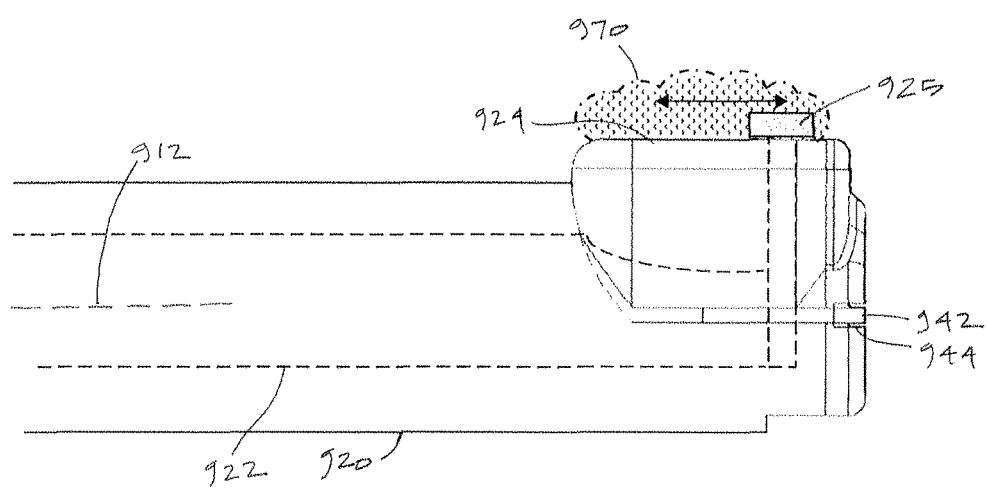
FIG. 27 is a schematic view of the working end of FIGS. 25-26 showing a plasma layer or cloud formed and maintained by RF energy delivery from the reciprocating electrode surface.

Referring to FIG. 27, it has been found that rapid reciprocation or oscillation of the electrode 915 in window 924 is very effective in a tissue ablation procedure, in part, because the ablative plasma practically forms a plasma layer or cloud 970 over the area of the window 922 even through the surface of the electrode 925 may be only in transient contact with a portion of the plasma cloud 970. The plasma layer or cloud is formed in an interface with targeted tissue wherein the plasma applies ablative energy to tissue as is known in the art. In an aspect of the invention shown in FIG. 27, a method (i) ignites a plasma in a conductive liquid in a tissue interface using RF energy delivered from an electrode surface 925, and (ii) moves the electrode surface 925 to form a plasma cloud 970 with a dimension that exceeds the area of electrode surface 925 wherein the rate of motion of the electrode surface delivers plasma-maintaining RF energy to the cloud 970 at a rater faster than the plasma cloud is extinguished in the conductive liquid. In a variation, the rate of motion of the electrode surface 925 is at least 0.2 msec. In other variations, the rate of motion is least 0.5 msec or at least 1.0 msec.

More in particular, referring to FIGS. 25-26, the electrode surface 925 moves in alignment with a longitudinal axis 912 of shaft 910 and window 924. The stroke of the electrode surface 925 has a dimension ranging between 1 mm and 10 mm, or more often, the stroke has a dimension ranging between 2 mm and 8 mm. The electrode surface 925 has a width WW dimension transverse to the axis of the stroke, with said width WW ranging between 1 mm and 10 mm, and more often between 2 mm and 8 mm (FIG. 25). In the variation shown in FIGS. 25-27, the window 924 in the ceramic body 915 has an area ranging from 5 mm$^2$ to 50 mm$^2$ and thus the plasma cloud 970 may have a surface area ranging from 5 mm$^2$ to 50 mm$^2$.

While the illustrated embodiment have and electrode that reciprocates in a predetermined cycles per second (Hz), it should be appreciated that electrode surface can be moved axially relative to the probe axis, or transverse relative to the probe axis, or can rotate relative to the probe axis. Thus, the needed rate of motion as described above can be provided by moving the electrode in any direction relative to the probe axis 912 to perform the method of the invention.

In general, a method for forming an RF plasma cloud for applying energy to tissue comprises immersing an electrode surface 925 in a conductive liquid in proximity to targeted tissue, and moving the electrode surface 925 over a selected cloud surface area while delivering electrical current to the moving electrode surface 925 such that a plasma cloud surface area is maintained although the electrode surface contacts only a portion of the cloud surface area at any point in time.

Another way to state the method for applying electrosurgical energy to tissue is immersing an electrode surface in a conductive liquid in proximity to targeted tissue and moving the electrode surface in a stroke at a selected Hz and applying an electrical current to the moving electrode surface adapted to form a transient plasma cloud thereabout which applies energy to the targeted tissue wherein the Hz rate is sufficiently fast to maintain the plasma cloud between the opposing ends of the stroke while the electrode surface is moving between said opposing ends of the stroke.

Referring again to the probes of FIGS. 18-22 and 23-25, a method of operating an electrosurgical probe comprises (i) providing an elongated shaft having a longitudinal axis, a windowed ceramic body carried at a distal end of the shaft, a moveable electrode surface disposed in the window, and a motor drive configured to move the electrode surface back and forth across the window, (ii) positioning the ceramic body and electrode surface in an interface with targeted tissue, and (iii) delivering an electrical current to the electrode and actuating the motor drive to move the electrode surface across the window at greater than 1 Hz or greater than 100 Hz to thereby ablate tissue in the interface. The targeted tissue is at least one of cartilage, meniscus, connective tissue, tendons, ligaments or synovial tissue.

In general, an RF probe corresponding to the invention comprises an elongated sleeve extending along a longitudinal axis with a windowed ceramic housing carried at a distal end of the sleeve and a motor-driven electrode surface configured to move across the window in the ceramic housing wherein a motor drive provides a rate of motion of the electrode surface of at least 0.2 m/sec, at least 0.5 m/sec or at least 1.0 m/sec. The window has an area of 5 mm$^2$ to 50 mm$^2$ and the electrode surface has an area of 1 mm$^2$ to 10 mm$^2$. The electrode surface can be moved across the window in a stroke having a dimension ranging between 1 mm and 10 mm, or more often ranging between 2 mm and 8 mm. The electrode surface can have a width dimension transverse to the axis of the stroke ranging between 1 mm and 10 mm, and more often between 2 mm and 8 mm. The ratio of the window area to the electrode surface area is at least 5:1 or at least 10:1.

Figure 28:
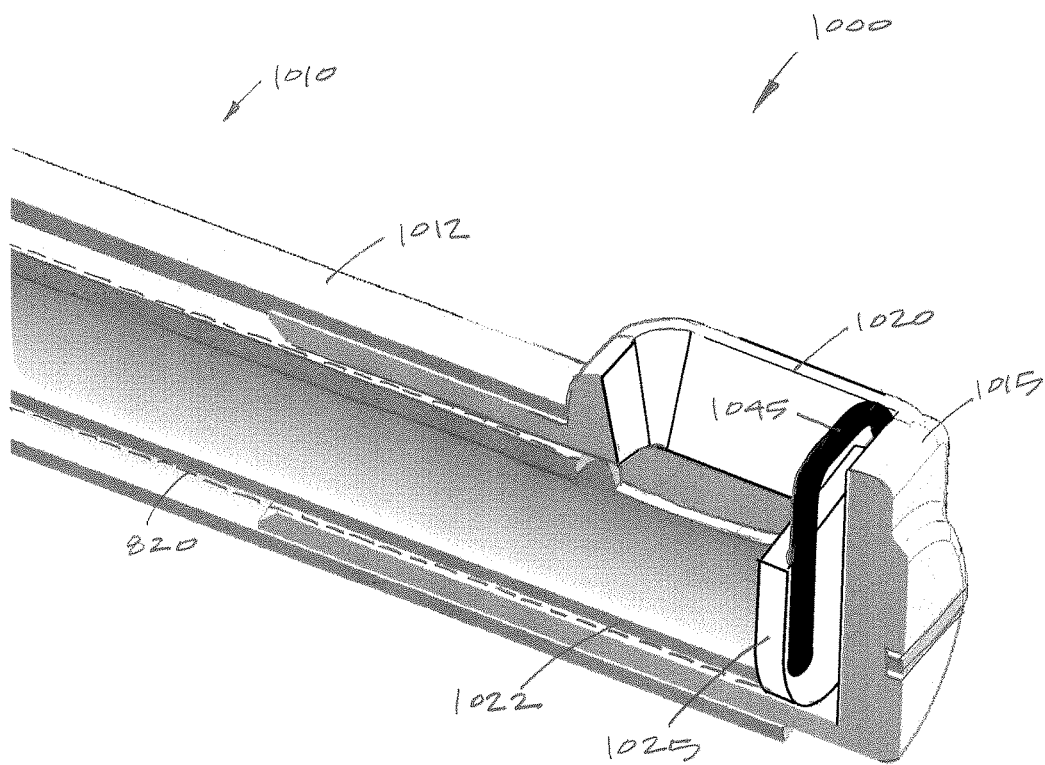
FIG. 28 is a perspective view of the working end and electrode of another variation of an RF probe similar to that of FIGS. 25-26.

FIG. 28 illustrates another variation of an RF probe 1000 that is similar to the version of FIGS. 25-26. The electrosurgical RF ablation probe 1000 is again is adapted for use with the handle 702 and motor drive unit 105 as shown in FIG. 23. In the variation shown in FIG. 28, the probe 1000 again has a shaft 1010 with an outer sleeve 1012 that carries a distal dielectric or ceramic housing 1015 with a window 1020 therein. The inner sleeve 1022 has a distal end on which a dielectric or ceramic member 1025 is mounted. In this variation, the electrode 1045 has a loop configuration which is adapted for cutting strips of tissue. Such a loop-shaped electrode can be adapted to reciprocate at high speeds as described above or can be moved in a single stroke for a slow, controlled resection of tissue. For example, in a mode of operation, a button on the handpiece or a footswitch could be actuated to cause a single reciprocation of the electrode together with actuation of the negative pressure source.

While the variations described above and shown in the drawings relate to RF probes that have an axially reciprocating electrode, it should be appreciated that a similar electrode can be configured to be driven laterally from side to side in a window of a ceramic housing carried at the distal end of an elongated. Such an RF probe can couple to the handpiece 702 and motor drive 105 as shown in FIG. 23.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An electrosurgical probe comprising:
an elongated shaft assembly having a proximal end, a distal end, and a longitudinal axis;
a housing carried on the distal end of the shaft;
an interior channel extending axially through the interior of the shaft and housing to an opening in the housing, said opening having a proximal edge; and
an electrode with an elongate edge extending laterally across the opening, said electrode configured to reciprocate longitudinally relative to the opening between a distally extended position and a proximally retracted position, wherein the elongate edge of the electrode extends over the proximal edge of the opening when the electrode is in the retracted position to shear tissue interfacing with the opening.

2. The electrosurgical probe of claim 1 wherein the shaft comprises an outer sleeve and an inner sleeve, wherein the housing is mounted on a distal end of the outer sleeve, the electrode is mounted on a distal end of the inner sleeve, and wherein the inner sleeve is reciprocatably mounted in the outer sleeve.

3. The electrosurgical probe of claim 2 further comprising a proximal hub attached to a proximal end of the outer sleeve and a sliding collar attached to a proximal end of the inner sleeve, said sliding collar being mounted to axially reciprocate within the proximal hub while being restrained from rotation relative to the proximal hub.

4. The electrosurgical probe of claim 3 further comprising a rotating coupling mounted to rotate in the proximal hub while being restrained from axially translating relative to the proximal hub, wherein the rotating coupling has a distal surface which engages a proximal surface on the sliding collar and wherein said distal and proximal surfaces are shaped so that rotation and/or rotational oscillation of the rotating coupling causes the sliding collar to axially reciprocate within the proximal hub to cause the electrode to axially reciprocate relative to the opening in the housing.

5. The electrosurgical probe of claim 1 wherein the electrode reciprocates with a stroke in a range from 0.01 mm and 10 mm.

6. The electrosurgical probe of claim 5 wherein the stroke is in a range between 0.1 mm and 5 mm.

7. The electrosurgical probe of claim 1 wherein the electrode has an outer surface that is outward of a plane of the opening.

8. The electrosurgical probe of claim 7 wherein the said outer surface extends outward of the plane of the opening by distance in a range from 0.50 mm to 2.5 mm.

9. The electrosurgical probe of claim 5 wherein the electrode has a proximally-facing edge that extends over an edge of the opening at an end of said stroke.

10. The electrosurgical probe of claim 5 wherein the electrode has lateral edges that extend over edges of the opening.

11. The electrosurgical probe of claim 4 further comprising a motor drive operatively coupled to the inner sleeve and configured to axially reciprocate the electrode.

12. The electrosurgical probe of claim 11 wherein the motor drive couples to the rotating coupling.

13. The electrosurgical probe of claim 11 wherein the motor drive is carried in a handpiece that is detachably coupled to the proximal hub.

14. The electrosurgical probe of claim 11 wherein the motor drive is configured to reciprocate the electrode at a rate in a range from 1 Hz and 1,000 Hz.

15. The electrosurgical probe of claim 13 further comprising a flow pathway that extends from a window section of the opening in the distal end of the inner sleeve to a side-facing opening in the rotating coupling.

16. An electrosurgical probe, comprising:
an elongated shaft carrying a distal dielectric housing, said elongated shaft having an interior channel extending to a window in the distal dielectric housing;
a dielectric member configured to move within the interior channel and window;
an electrode carried by the dielectric member, wherein said electrode has an edge which extends laterally across the window and over a proximal edge of the window to resect tissue interfacing with the window; and
a motor operatively coupled to the dielectric member to axially reciprocate the dielectric member to move the electrode in the window.

17. The electrosurgical probe of claim 16 wherein the dielectric housing is a ceramic material.

18. The electrosurgical probe of claim 16 wherein the moveable dielectric member is a ceramic material.

19. The electrosurgical probe of claim 16 further comprising a negative pressure source communicating with said interior channel.

20. The electrosurgical probe of claim 16 wherein the shaft comprises an outer sleeve and an inner sleeve, wherein the dielectric housing is carried by a distal end of the outer sleeve, the moveable dielectric member is mounted on a distal end of the inner sleeve, and wherein the inner sleeve is reciprocatably mounted in the outer sleeve.

21. The electrosurgical probe of claim 16 wherein the electrode has an outer surface that is outward of a plane of the window.

22. The electrosurgical probe of claim 16 wherein the said outer surface extends outward of the plane of the window by distance in a range from 0.50 mm to 2.5 mm.

23. The electrosurgical probe of claim 16 wherein the electrode has edges that extend over an edge of the window.

24. A method for ablating tissue, said method comprising:
engaging a window having a planar opening with a proximal edge in a housing against a surface of the tissue;
axially reciprocating a lateral elongate edge of a member across the window in a plane parallel to the plane of the window;
applying a radiofrequency current to the lateral elongate edge; and
applying a vacuum to the housing;
wherein the lateral elongate edge extends over an edge of the opening at a proximal end of its reciprocation to shear tissue interfacing with the window.

25. The method of claim 24 wherein the elongate edge protrudes beyond the plane of the window in the housing.

26. The method of claim 25 wherein the elongate edge protrudes beyond the plane of the window in the housing by a distance in the range from 0.50 mm to 2.5 mm.

27. The method of claim 24 wherein the elongate edge is reciprocated at a rate in a range from 1 Hz and 1,000 Hz.

28. The method of claim 24, wherein the applying the radiofrequency current to the lateral elongate edge ablates tissue and generates tissue debris.

29. The method of claim 28, wherein applying the vacuum to the housing aspirates the tissue debris.

* * * * *